US008322336B2

(12) United States Patent
Pocock et al.

(10) Patent No.: US 8,322,336 B2
(45) Date of Patent: Dec. 4, 2012

(54) FLUID-PRODUCT DISPENSING DEVICE

(75) Inventors: Andrew Gordon Pocock, Ickleton (GB); Stuart Brian William Kay, Ickleton (GB); Paul Greenhalgh, Ickleton (GB); Wayne O'Hara, Ickleton (GB); Xavier Donnette, Plaisir (FR)

(73) Assignee: Aptar France SAS, Le Neubourg (FR)

( * ) Notice: Subject to any disclaimer, the term of this patent is extended or adjusted under 35 U.S.C. 154(b) by 759 days.

(21) Appl. No.: 12/374,914

(22) PCT Filed: Jul. 17, 2007

(86) PCT No.: PCT/FR2007/051670
§ 371 (c)(1),
(2), (4) Date: Jan. 23, 2009

(87) PCT Pub. No.: WO2008/012456
PCT Pub. Date: Jan. 31, 2008

(65) Prior Publication Data
US 2009/0308389 A1    Dec. 17, 2009

(30) Foreign Application Priority Data
Jul. 25, 2006  (FR) ..................................... 06 53101

(51) Int. Cl.
*A61M 16/00*   (2006.01)
*B05D 7/14*    (2006.01)
*B65D 83/06*   (2006.01)

(52) U.S. Cl. ......... 128/203.15; 128/203.12; 128/200.23; 128/203.21; 128/203.19; 128/203.2; 222/402.2

(58) Field of Classification Search ............... 222/402.2; 128/203.12, 200.23, 200.14, 203.21, 203.19, 128/203.23
See application file for complete search history.

(56) References Cited

U.S. PATENT DOCUMENTS

| 6,012,454 A | 1/2000 | Hodson et al. |
| 6,880,555 B1 * | 4/2005 | Brunnberg et al. ...... 128/203.12 |
| 2005/0081851 A1 | 4/2005 | Young et al. |

FOREIGN PATENT DOCUMENTS
WO     2006/071512 A1    7/2006

* cited by examiner

*Primary Examiner* — Lynne Anderson
*Assistant Examiner* — Bradley Philips
(74) *Attorney, Agent, or Firm* — Sughrue Mion, PLLC

(57) ABSTRACT

An inhaler comprising: at least one cover element (11, 12); individual reservoirs formed on a substrate; support means (50) that are movable between a non-dispensing position and a dispensing position; reservoir-opening means (80); displacement means (30) for displacing said reservoir substrate in a first direction, said reservoir substrate also being displaceable between said non-dispensing position and said dispensing position in which said opening means open a respective reservoir; loading means (51) for urging said movable support means towards said dispensing position; blocking means (100) for retaining said movable support means in the non-dispensing position; trigger means (60) that are actuated by inhalation; and connection means (1000) for displacing said reservoir substrate in said first direction when said at least one cover element is displaced, said connection means being activated while said movable support means are being displaced towards said dispensing position while the user is inhaling, and being deactivated in the absence of any inhalation.

13 Claims, 31 Drawing Sheets

FLUID-PRODUCT DISPENSING DEVICE

The present invention relates to a fluid dispenser device, and more particularly to a dry-powder inhaler.

Dry-powder inhalers are well known in the prior art. Various types exist. A first type of inhaler contains a reservoir receiving many doses of powder, the inhaler being provided with metering means making it possible, on each actuation, to remove one dose of said powder from the reservoir, so as to bring said dose into an expulsion duct in order to be dispensed to the user. Another type of inhaler consists in packaging the doses of powder in individual predosed reservoirs, then in opening one of the reservoirs each time the inhaler is actuated. That implementation seals the powder more effectively since each dose is opened only when it is about to be expelled. In order to make such individual reservoirs, various techniques have already been proposed, such as an elongate blister strip or blisters disposed on a rotary circular disk. Inhalers including individual reservoirs, such as capsules, that are loaded into the inhaler just before said reservoir is used are also described in the prior art. The advantage of such devices is that it is not necessary to store all of the doses inside the appliance, such that said appliance can be compact. Obviously however, the inhaler is more difficult to use, since the user is obliged to load a capsule into the inhaler before each use. All existing types of inhalers, including those described above, present both advantages and drawbacks associated with their structures and with their types of operation. Thus, with certain inhalers, there is the problem of accuracy and of reproducibility for the dose on each actuation. In addition, the effectiveness of the dispensing, i.e. the fraction of the dose that effectively penetrates into the user's lungs in order to have a beneficial therapeutic effect, is also a problem that exists with a certain number of inhalers. A solution for solving that specific problem has been to synchronize the expulsion of the dose with the inhalation of the patient. Once again, that can create drawbacks, in particular in that type of device, the dose is generally loaded into an expulsion duct before inhalation, then expulsion is synchronized with inhalation. That means that if the user drops, shakes, or manipulates the inhaler in an undesirable or inappropriate manner between the moment when the user loads the dose (either from a multidose reservoir or from an individual reservoir) and the moment when the user inhales, then the user risks losing all or part of the dose, with said dose possibly being spread about inside the appliance. In that event, there can exist a high risk of overdosing the next time the device is used. The user who realizes that the dose is not complete will load a new dose into the appliance, and while the new dose is being inhaled, a fraction of the previous dose that was lost in the appliance could thus be expelled at the same time as the new dose, thereby causing an overdose. In the treatments envisaged, such overdosing can be very harmful, and the authorities in all countries are issuing ever-stricter requirements to limit the risk of overdosing as much as possible. With regard to opening the individual reservoirs, it has been proposed to peel off or to unstick the closure layer. That presents the drawback of difficulty in controlling the forces to be applied in order to guarantee complete opening, without running the risk of opening the next reservoir, particularly if the opening means need to be actuated by inhalation. In a variant, it has been proposed to perforate the closure layer or wall. That presents the drawback that the cut wall-portions risk retaining a fraction of the dose inside the reservoir, so that metering accuracy and reproducibility are therefore not guaranteed.

An object of the present invention is to provide a fluid dispenser device, in particular a dry-powder inhaler, that does not have the above-mentioned drawbacks.

In particular, an object of the present invention is to provide a device that is simple and inexpensive to manufacture and to assemble, that is reliable in use, guaranteeing metering accuracy and metering reproducibility on each actuation, providing an optimum yield with regard to the effectiveness of the treatment, by making it possible to dispense a substantial fraction of the dose to the zones to be treated, in particular the lungs, avoiding, in safe and effective manner, any risk of overdosing, and that is as compact as possible, while guaranteeing sealing and absolute integrity of all of the doses up to their expulsion.

Another object of the present invention is to provide a device that avoids any risk of under-dosing, with the reservoir being opened, the dose being expelled, and the emitted dose being counted only after the user has inhaled. In addition, an object of the present invention is to avoid any risk of doses being lost in the absence of any inhalation, even if the user manipulates the device.

Another object of the present invention is to provide a device that makes it possible to count the number of doses that have been emitted or that remain to be emitted.

The present invention thus provides a fluid dispenser device, comprising: a body provided with a dispenser orifice; at least one cover element that is movable between a closed position and an open position; a plurality of individual reservoirs each containing a dose of fluid, such as a pharmaceutical powder, said reservoirs being formed on a reservoir substrate; movable support means that receive said reservoir substrate, and that are displaceable between a non-dispensing position and a dispensing position; reservoir-opening means for opening a respective reservoir each time said opening means are actuated; displacement means for displacing said reservoir substrate in a first direction so as to bring a full reservoir into register with said opening means after each use of the device, said reservoir substrate also being displaceable, together with the movable support means, between said non-dispensing position, in which it does not co-operate with said opening means, and said dispensing position, in which said opening means open a respective reservoir; loading means for urging said movable support means towards said dispensing position, said loading means being loaded by said at least one cover element; blocking means for retaining said movable support means in the non-dispensing position; trigger means for releasing said blocking means and for enabling said movable support means, and thus said reservoir substrate, to be displaced towards said dispensing position, said trigger means being actuated by the user inhaling; connection means which, when they are activated, connect said displacement means with said at least one cover element, so as to displace said reservoir substrate in said first direction when said at least one cover element is returned from its open position to its closed position; and said connection means being activated while said movable support means are being displaced towards said dispensing position while the user is inhaling, and being deactivated in the absence of any inhalation, such that opening said at least one movable cover and then closing it without inhaling does not displace said reservoir substrate in said first direction.

The present invention also provides a fluid dispenser device, comprising: a body provided with a dispenser orifice; at least one cover element that is movable between a closed position and an open position; a plurality of individual reservoirs each containing a dose of fluid, such as a pharmaceutical powder, said reservoirs being formed on a reservoir substrate;

movable support means that receive said reservoir substrate, and that are displaceable between a non-dispensing position and a dispensing position; reservoir-opening means for opening a respective reservoir each time said opening means are actuated; displacement means for displacing said reservoir substrate in a first direction so as to bring a full reservoir into register with said opening means before each use of the device, said reservoir substrate also being displaceable, together with the movable support means, between said non-dispensing position, in which it does not co-operate with said opening means, and said dispensing position, in which said opening means open a respective reservoir; loading means for urging said movable support means towards said dispensing position, said loading means being loaded by said at least one cover element; blocking means for retaining said movable support means in the non-dispensing position; trigger means for releasing said blocking means and for enabling said movable support means, and thus said reservoir substrate, to be displaced towards said dispensing position, said trigger means being actuated by the user inhaling; connection means which, when they are activated, connect said displacement means with said at least one cover element, so as to displace said reservoir substrate in said first direction when said at least one cover element is brought from its closed position to its open position; and said connection means being deactivated while said movable support means are being displaced towards said dispensing position while the user is inhaling, and being activated in the absence of any inhalation, such that opening said at least one movable cover element and then closing it without inhaling displaces said reservoir substrate in said first direction while the cover element is being opened, and returns said reservoir substrate in the opposite direction into its initial position while the cover element is being closed.

Advantageously, said reservoir-opening means are perforator means that do not move relative to the dispenser orifice.

Advantageously, said reservoir substrate is a blister strip, with the reservoirs being formed by blisters disposed one behind another along said strip.

Advantageously, said reservoir substrate co-operates with a recessed wheel having recesses for receiving said reservoirs, said wheel being displaceable in turning so as to displace said reservoir substrate in said first direction in order to bring a full reservoir into register with the reservoir-opening means before and/or after each inhalation, and being displaceable towards said reservoir-opening means when the user inhales, in order to open said reservoir.

Advantageously, said recessed wheel is displaceable relative to the reservoir-opening means between a non-dispensing position and a dispensing position in which said reservoir-opening means penetrate into a reservoir, said recessed wheel being resiliently urged towards the dispensing position and being retained in its non-dispensing position by blocking means, said blocking means being connected to a movable member that is displaced during inhalation so as to release said blocking means.

Advantageously, said recessed wheel includes a first set of teeth that co-operates with a drive element that is connected to at least one movable cover element.

Advantageously, said loading means engage said first set of teeth with said drive element when they are activated, and disengage said first set of teeth from said drive element when they are deactivated.

Advantageously, a drive element is pivotally mounted on the body, said drive element including a first projection that co-operates with said recessed wheel, and a second projection that co-operates with a loading member that is connected to said at least one movable cover element.

Advantageously, said loading member is pivotally mounted on the body and includes: engagement means connected to said at least one movable cover element; and guide means, such as a groove, for receiving and guiding said second projection of said drive element.

Advantageously, said groove comprises at least two groove portions, a first portion and a second portion of different inclinations, said drive element being pivoted relative to said body, only while said second projection is co-operating with said second groove portion.

These characteristics and advantages and others of the present invention appear more clearly from the following detailed description of several embodiments and variants thereof, given by way of non-limiting example, and with reference to the accompanying drawings, in which.

Figure 1:
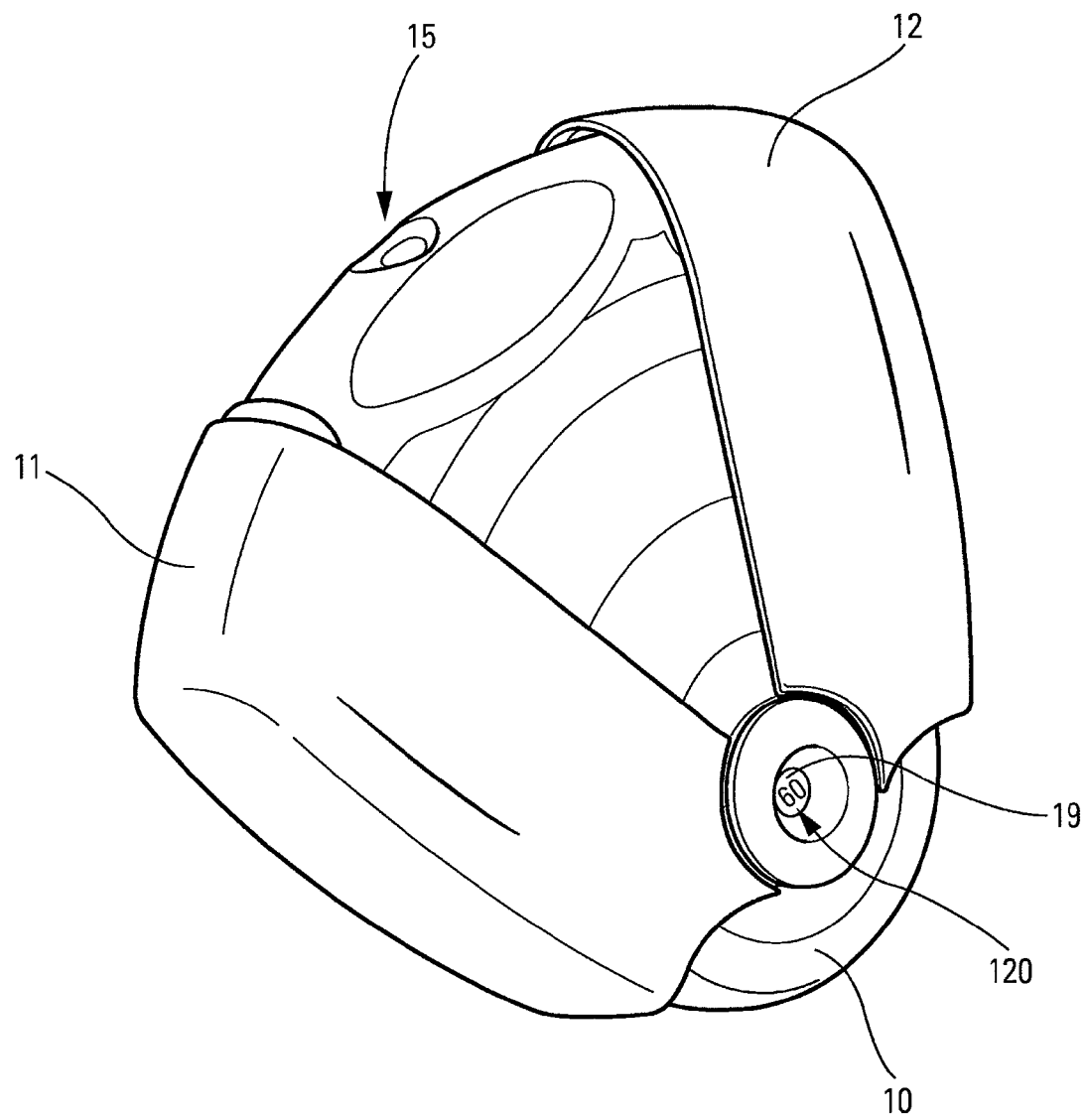
FIG. 1 is an external diagrammatic view of a device constituting an advantageous variant of the invention.

FIG. 1 shows an external view of an embodiment of a dry-powder inhaler. The inhaler comprises a central body 10 on which there are slidably mounted two lateral elements or wings 11, 12 that form a cover when the device is closed and that are adapted to be moved apart in order to open the device and thus stress the device as described below. The body 10 can be approximately rounded in shape at its bottom portion, and relatively flat at its top portion, as shown in the FIG. 1, but it could be of any other appropriate shape. The body 10 includes a dispenser and inhaler orifice 15 through which the user inhales while the device is being actuated. The two cover-forming lateral portions 11, 12 can be opened by pivoting about a common pivot axis as shown in FIG. 1, but any other opening means can be envisaged for opening the device. Alternatively, it is possible to provide only one cover element that is movable relative to the body, instead of the two shown in FIG. 1.

Figure 32:
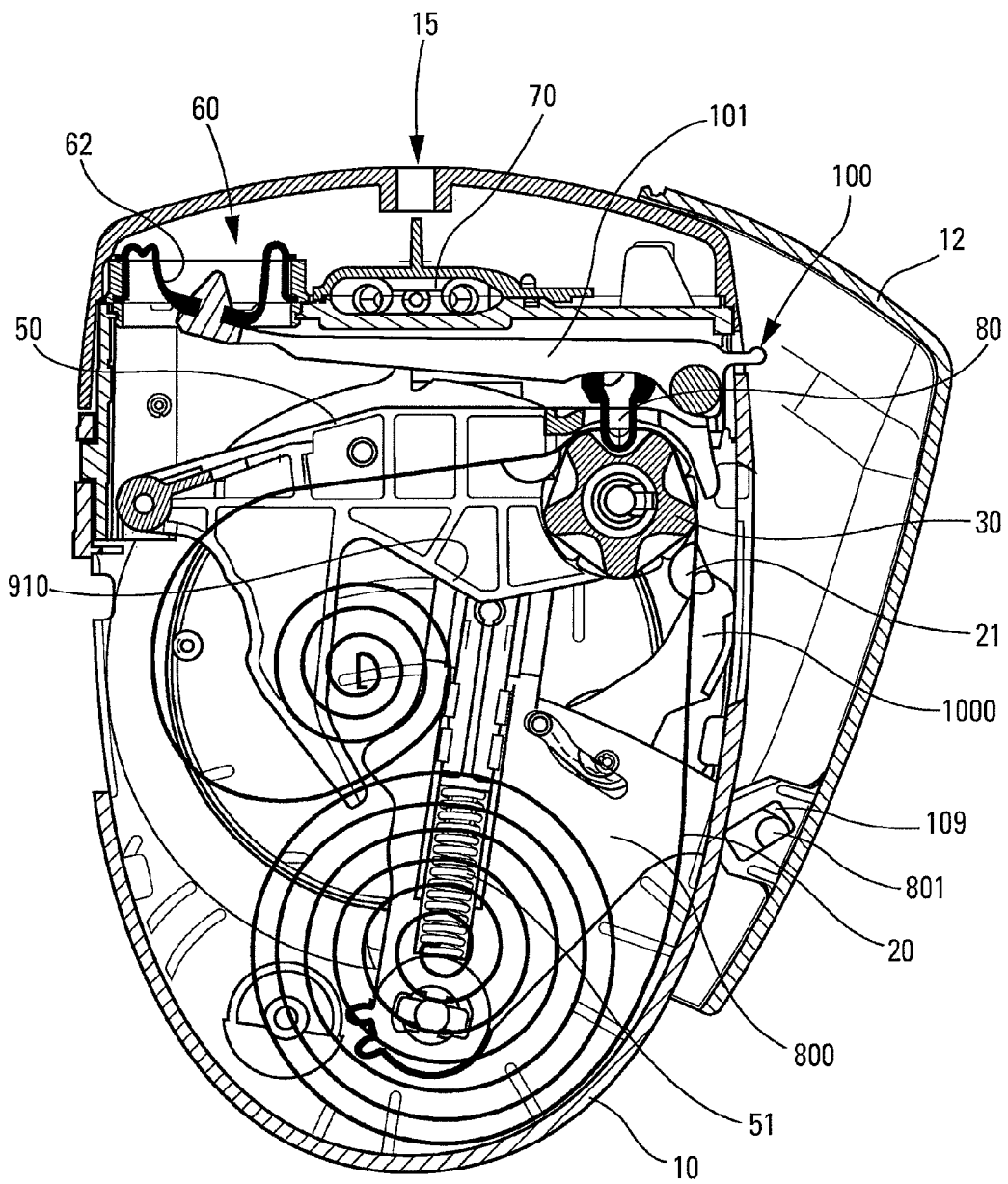
FIG. 32 is a view similar to the view in FIG. 5, diagrammatically showing the reservoir substrate and the opening means constituting an advantageous variant of the invention.

The body advantageously includes a window 19 through which the count of the doses that have been dispensed or that remain to be dispensed can be displayed in visible manner for the user. The window 19 can advantageously be provided on or close to the pivot axis of the cover-forming cover elements 11, 12. A substrate 20 of individual reservoirs 21 can be provided inside the body. The reservoirs are advantageously of the blister type, and the reservoir substrate is preferably an elongate strip on which the blisters are disposed one behind another, in known manner. The strip and the blisters are shown in part in FIG. 32 only so as not to overload the other drawings for the purpose of clarity. The blister strip may advantageously be constituted by a base layer or wall that forms cavities receiving the doses of powder, and by a closure layer or wall that covers each of said blisters in sealed manner. The blister strip can be rolled-up inside the body, and drive means 30 for driving the strip are provided for progressively unrolling the blister strip and for bringing a respective blister or individual reservoir into a dispensing position each time the device is actuated. When an individual reservoir has been emptied by inhalation, the strip portion that includes said empty reservoirs is advantageously adapted to be rolled-up at another location of said body 10.

Reservoir-opening means 80 are provided in, or secured to, the body 10, the opening means comprising perforator and/or cutter means for perforating or cutting the closure layer of the blisters. The opening means are also shown diagrammatically in FIG. 32 only so as not to overload the other drawings for the purpose of clarity.

Movable support means 50 are adapted to support at least the reservoir that is to be opened during the next inhalation. The movable support means 50 are adapted to displace the reservoir to be emptied against said opening means of the device during actuation. Advantageously, the movable support means 50 are urged by an elastically-deformable loading element, such as a spring, a rod, or any other equivalent resilient element, said loading element being suitable for being prestressed in particular while the device is being opened. Advantageously, the movable support means 50 are displaceable between a first position (a non-dispensing position) and a second position (a dispensing position) that is the position for opening the reservoir.

The movable support means 50 advantageously comprise a substantially rigid part, such as a rod, that is hinged relative to said body 10. A guide wheel 30 that is fastened in rotary manner on said movable support means 50 receives and guides the blisters. Turning the guide wheel 30 thus causes the blister strip to advance in a first direction. In a particular angular position, a given reservoir or blister is always in position to be opened by the opening means. Advantageously, rotary positioning means 300 for positioning said guide wheel 30 in turning can be provided for accurately determining the angular position of said guide wheel 30 after each turn. In an advantageous variant, the positioning means 300 can comprise a projection or finger 301 having an end that co-operates resiliently with notches 38 that are provided around said guide wheel 30. Advantageously, the notches 38 have an approximately V-shaped profile that automatically guides said finger 301 towards the central position of the notch, thereby guaranteeing accurate angular positioning at each turn. The positioning means 300 are visible in FIGS. 2 and 6 in particular. The guide wheel 30 preferably forms the only drive means for driving the reservoir substrate. One (or more) additional wheel(s) could optionally be provided so as to help guide and/or drive the reservoir substrate.

Figure 5:
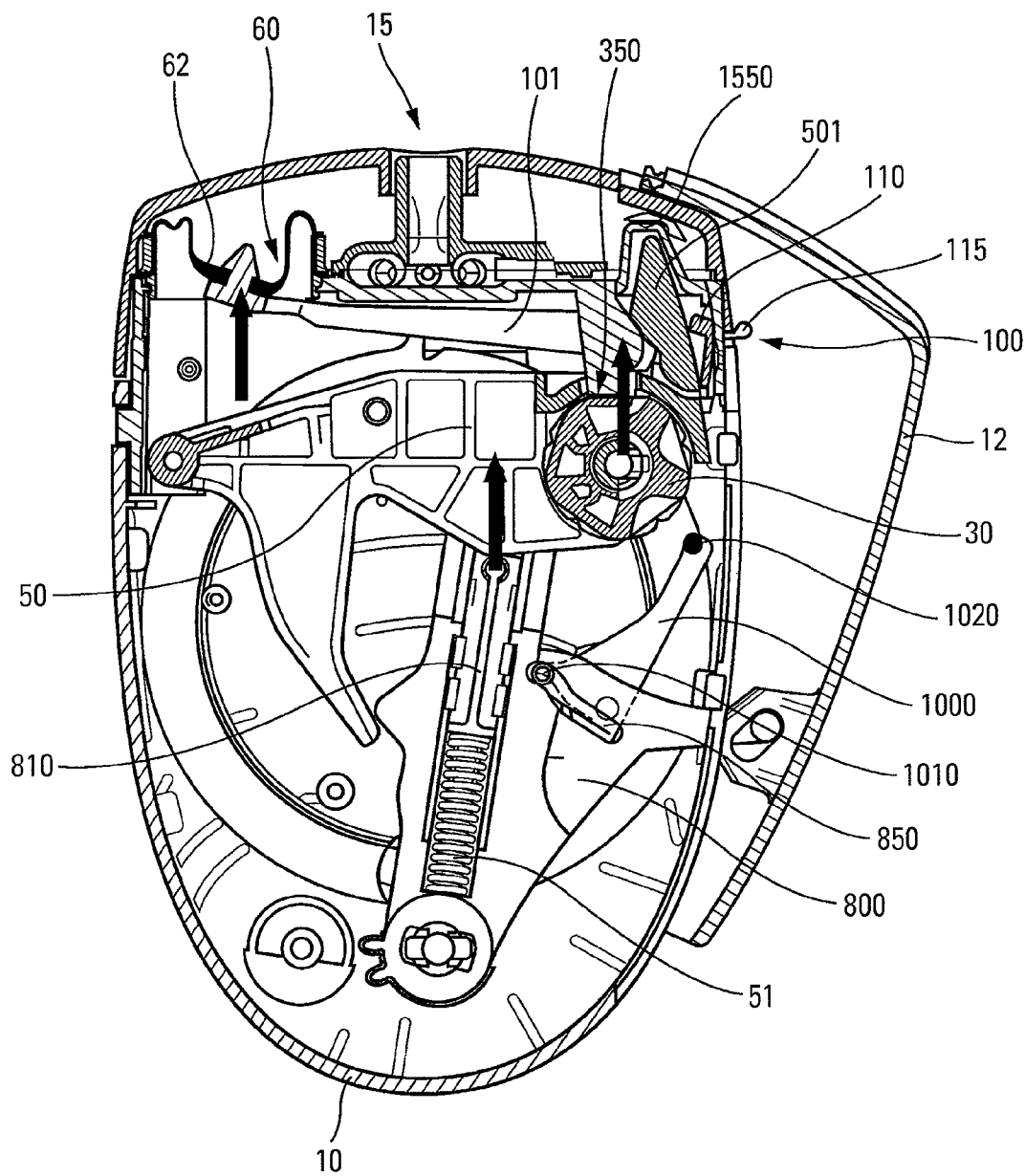
FIG. 5 is a view similar to the view in FIG. 4, shown after inhalation.

Advantageously, abutment means 350 are provided for accurately determining the dispensing position of the guide wheel 30 during each inhalation. The abutment means can comprise a lug 350 that is adapted to co-operate, when in the dispensing position, with one or more corresponding plane surfaces of the guide wheel 30. Preferably, one plane surface is associated with each recess. In this embodiment, the abutment 350 contributes to correct rotary positioning of the guide wheel 30 when the opening means, in particular the perforator and/or cutter means penetrate into the reservoir to be emptied. The abutment 350 therefore defines not only the depth to which said perforator and/or cutter means penetrate into the reservoir, but also their centering relative to the reservoir, so as to guarantee optimum expulsion of the powder and reproducibility of the dose taken on each actuation. The abutment means 350 can be associated with the above-mentioned rotary positioning means 300, in such a manner as to predetermine in accurate manner each position of the guide wheel, in the non-dispensing position, in the dispensing position, and also while the guide wheel 30 is being displaced between said positions. This makes it possible to avoid any risk of the device blocking in the event of said guide wheel being badly positioned. The abutment means 350 are shown in FIG. 5 in particular.

While the reservoir is being displaced towards its opening position in order to be opened by the opening means 80, the opening means are preferably stationary relative to the body 10. However, it is possible to envisage that the opening means could also move during the step of opening the reservoir. For example, the opening means could be displaced towards the reservoir while the reservoir is being displaced towards the opening means. In another variant, it is also possible to envisage that the reservoir and the opening means are displaced in the same direction during actuation, the reservoir being displaced more quickly in said direction, such that it comes into contact with said opening means in order to be opened.

As explained above, it is desirable for the opening means to be actuated by the user inhaling. In order to trigger the reservoir-opening means by inhalation, an inhalation trigger system is provided that advantageously comprises means 60 that are displaceable and/or deformable under the effect of inhalation, the means 60 being adapted to release the blocking means 100. The means 60 advantageously comprises a deformable air-chamber 61 that co-operates with the blocking means 100 of said movable support means 50. Inhalation by the user causes said deformable air-chamber 61 to deform, thereby making it possible to release said blocking means 100 and therefore unblock the movable support means 50, so as to make it possible to displace the guide wheel 30, and thus the reservoir to be emptied, towards its opening position. Advantageously, the air chamber 61 can comprise a deformable membrane 62, that can be connected firstly to the inhaler orifice 15, and secondly to said blocking means 100 in direct or indirect manner. Thus, during inhalation, the membrane 62 deforms and/or contracts, thereby causing said blocking means 100 to be displaced into an unblocking position. Advantageously, a pouch or diaphragm 62 can form the air chamber 61. The pouch 62 is connected to the inhaler orifice 15 via a channel 151 that is advantageously disposed around an expulsion channel 152 that is connected to a dispenser chamber 70. The pouch 62 may be fastened to a rod 101 that is connected to the blocking means 100, inhalation causing the pouch 62 to deform thereby causing the rod 101 to pivot in order to displace said blocking means 100. The pouch 62 may advantageously be made of silicone, and may include a hem 620 that is adapted to form a seal with the body 10. To do this, the hem 620 can be extended by a flange 625, also made of silicone, that becomes compressed by a snap-fastener portion of the body 10 in order to achieve sealing, and in particular to avoid any head loss in the inhalation flow. In a variant, the deformable air chamber could be made in some other way, in particular by any deformable membrane.

The inhaler further includes a dispenser chamber 70 for receiving the dose of powder after a respective reservoir has been opened. The dispenser chamber 70 is advantageously provided with at least one substantially spherical element 75, such as a bead, that is displaced inside said chamber 70 during inhalation so as to improve dispensing of the air and powder mixture after a reservoir has been opened, in order to increase the effectiveness of the device.

In a particular variant, the deformable air-chamber 61 co-operates with the dispenser chamber 70. The dispenser chamber 70 can therefore be connected to the opening means of the reservoir, and in particular to the perforator and/or cutter means, and can include a dispenser orifice 79, advantageously connected directly to the dispenser and inhaler orifice 15 of the device. The membrane 62 can thus be connected firstly to the inhaler orifice 15, and secondly to the dispenser chamber 70, in the user's inhalation flow path. It can be advantageous for the opening means, in particular for the perforator and/or cutter means, to be formed directly on said dispenser chamber 70, e.g. at the end of a channel 69 leading to said chamber 70.

After inhalation, when the user closes the device, all of the components return to their initial, rest position, i.e. the movable support means 50 pivot about their pivot axis to return to their non-dispensing position by moving away from the reservoir-opening means, and the load element is also returned to its initial rest position in which it is not compressed or deformed. The device is thus ready for a new utilization cycle.

In a variant, other inhalation trigger means could also be used, e.g. using a pivotable valve flap that, while the user is inhaling, pivots under the effect of the suction created by the inhalation, with pivoting of the valve flap causing the blocking means blocking the movable support means to be released, thereby causing the reservoir to be displaced towards the opening means.

Figure 2:
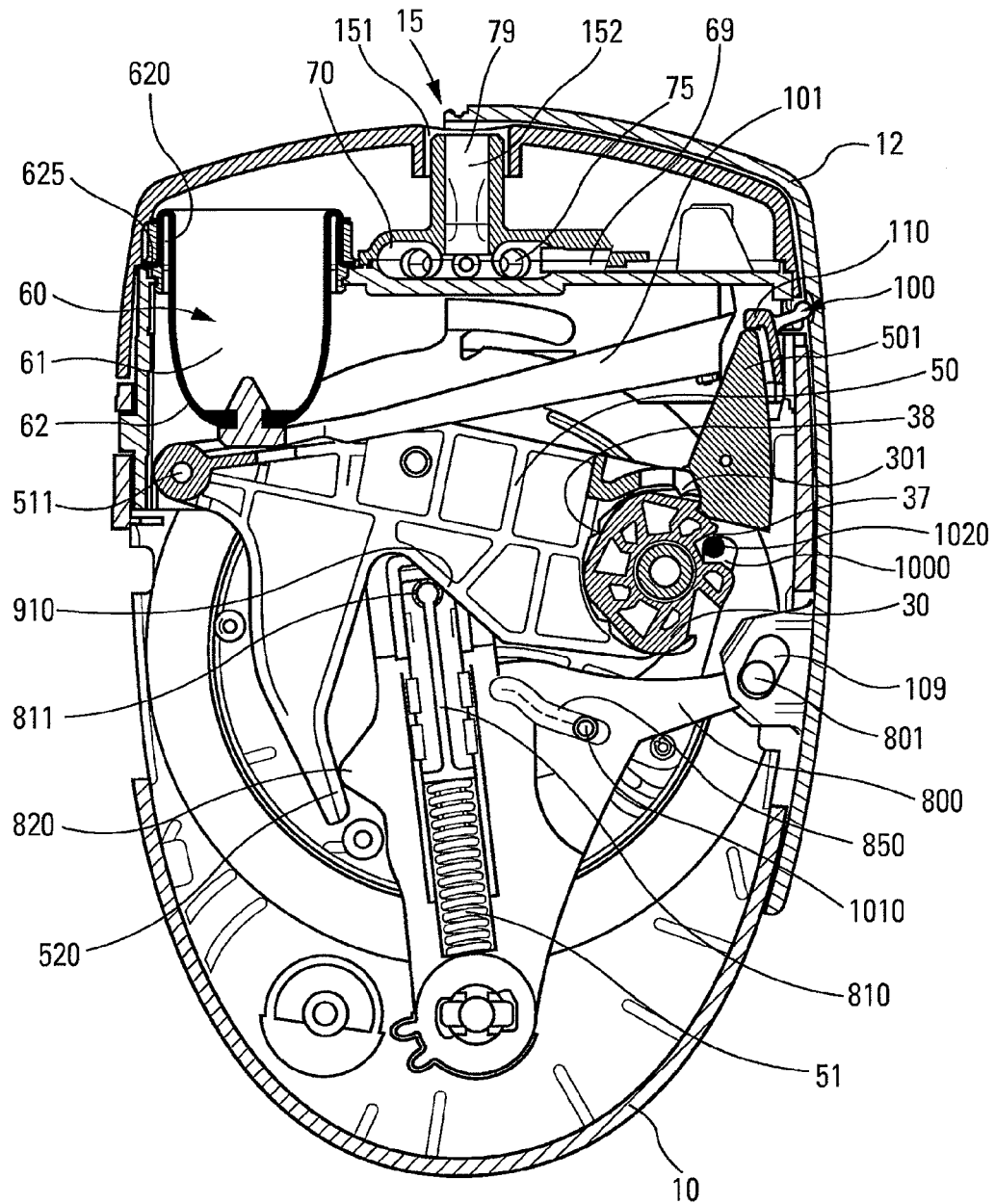
FIG. 2 is a diagrammatic section view of a device constituting an embodiment of the invention, shown in the closed position.
Figure 3:
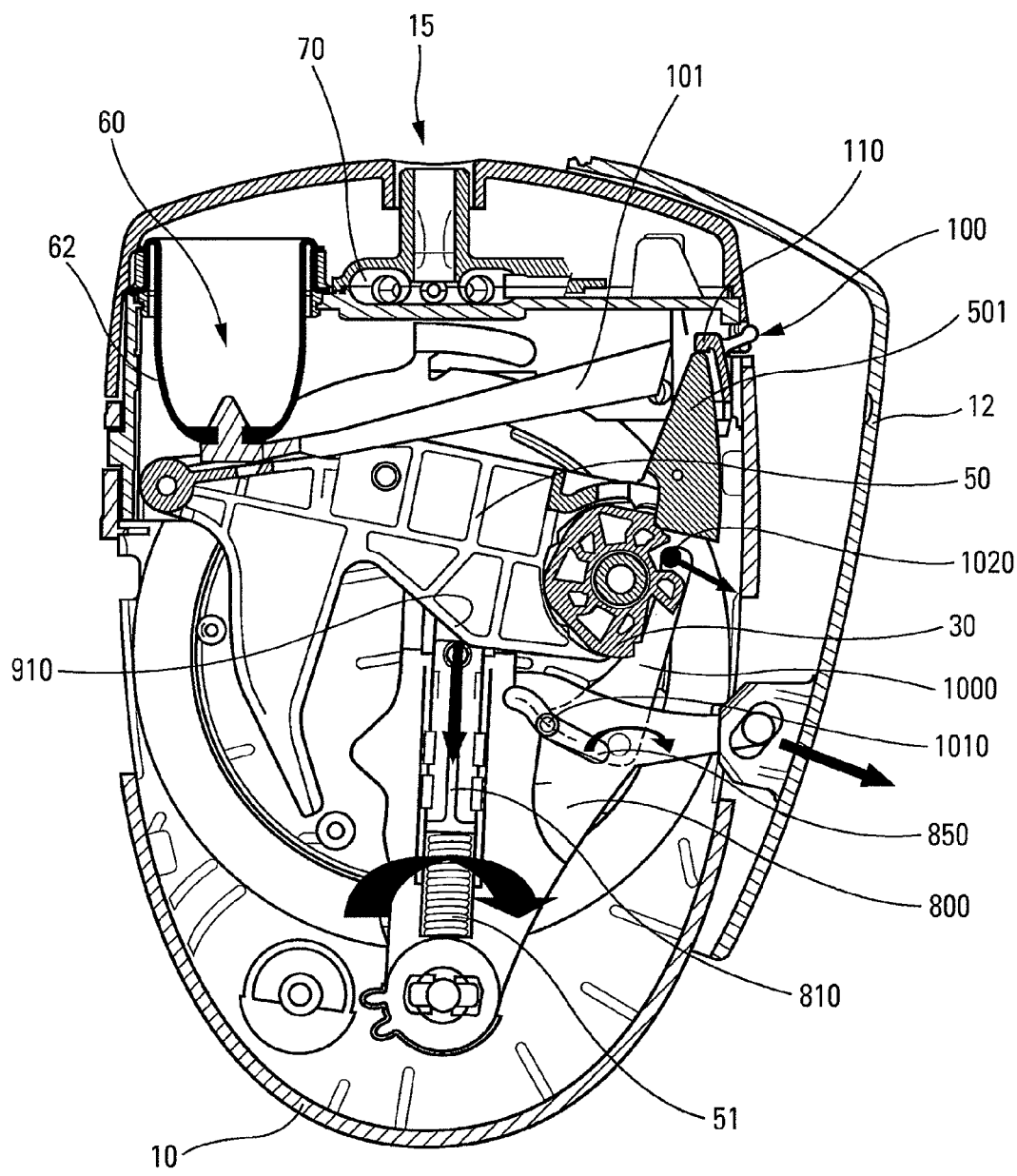
FIG. 3 is a view similar to the view in FIG. 2, shown during opening.

The movable support means 50 that support the guide wheel 30 may advantageously include an extension 501, indicated in FIGS. 2 and 5, that serves in particular to co-operate with the blocking means 100. Furthermore, the extension may also serve to substantially block a hole 1550 provided in the device, when the movable support means are in the dispensing position. In the non-dispensing position, the inhalation flow thus passes in part via the hole 1550. After the movable support means 50 are displaced into the dispensing position, thereby causing the hole 1550 to be blocked substantially and the reservoir to open, the inhalation flow is channeled mainly towards said open reservoir. This improves effectiveness during inhalation and helps to ensure that the reservoir is emptied in optimum manner.

In another advantageous aspect of the inhaler, the individual reservoirs or blisters 21 are formed on an elongate strip 20 that is stored in the form of a roll inside the body 10 of the device. Advantageously, the rolled-up blister strip is held by inner walls of said body 10 without its "rear" end (rear in the displacement direction of the blister strip) being fastened relative to said body 10, thereby enabling the blister strip to be assembled more easily inside the device. The blister strip is advantageously displaced by means of the guide wheel 30 that advantageously presents at least one and preferably more recesses 31, shown in FIG. 6, having a shape that corresponds substantially to the shape of the blisters. Thus, when the guide wheel 30 turns, it drives the blister strip in the first direction. Naturally, in a variant or in additional manner, it is possible to use other means for advancing the blister strip, e.g. providing a profile on the longitudinal lateral edges of the blister strip, said profile being adapted to co-operate with appropriate drive means. In addition, holes formed along the lateral edges of the blister strip could also be used to cause the blister strip to advance by means of toothed wheels co-operating with said holes, as with photographic film.

In still another aspect of the inhaler, a dose counter or indicator device is also provided. The device may include numbers or symbols that are marked directly on the blister strip, and that are visible through an appropriate window in the body of the device. In a variant, it is possible to envisage using one or more rotary disks including numbers or symbols, as described below.

FIGS. 2 to 9 show an advantageous embodiment of the present invention. With reference to this embodiment, the device includes a body 10 on which two cover elements 11, 12 are advantageously hinged about a common hinge axis, as shown in FIG. 1. For the purpose of clarity, only one of the cover elements, specifically the cover element shown on the righthand side of the device and indicated by numerical reference 12, is shown in the figures. The displacements of the various parts are indicated diagrammatically by arrows in certain figures.

Said movable cover element 12 is connected to a cocking member 800, advantageously via an opening 109 that may be oblong in shape and in which there is received a lug 801, or the like, of said cocking member 800. Advantageously, the cocking member 800 is pivotally mounted on the body 10 about a pivot axis. The cocking member 800 supports the loading element 51 that, in this embodiment, is made in the form of a helical spring. The spring 51 co-operates with a rod 810, connected at one end to said helical spring 51 and at its other end to a cam surface 910 provided on said movable support means 50, said rod being described below. While the cocking member 800 is being displaced about its pivot axis during displacement of the movable cover element 12, the rod 810 is thus adapted to compress the spring 51 when the cover element 12 is open, and to decompress said spring 51 when said cover element 12 is closed. In its portion in contact with the cam surface 910, the rod 810 advantageously includes a rounded portion 811, such as a ball-shaped end, to encourage the rod 810 to slide over said cam surface 910. The cocking member 800 further includes a projection 820 that is adapted to co-operate with an extension portion 520 of the movable support means 50, as described in more detail below. The cocking member 800 further includes guide means 850, advantageously formed in the form of a groove in which there is received a projection 1010 that is connected to a drive element 1000, that is also described in more detail below. Advantageously, said groove 850 comprises at least two portions of different slopes, having functions that are also described below.

In this embodiment, the movable support means 50 are made in the form of a part that is pivotally mounted on the body about a pivot axis 511. The movable support means 50 also incorporate an extension 501, advantageously in the shape of a fin. The above-mentioned cam surface 910 is formed on said movable support means 50 so that when the spring 51 is loaded while opening the movable cover element 12, said movable support means 50 are urged towards their dispensing position by said rod 810 being thrust by the compressed spring 51. Blocking means 100 are provided for retaining said movable support means 50 in said non-dispensing position, shown in particular in FIG. 2. Said blocking means 100 advantageously include a blocking element 110 that is adapted to co-operate with said extension 501 of said movable support means 50. Said blocking means 100 are advantageously connected by means of a rod 101 to the deformable diaphragm 62 that is sensitive to inhalation by the user, so that while the user inhales, said diaphragm deforms, thus causing the rod 101 to pivot, and consequently said blocking element 110, thereby releasing the extension 501. This enables said movable support means 50 to be displaced towards their dispensing position under the effect of the force exerted by the compressed spring 51. The displacement of the movable support means 50 causes an individual reservoir to be opened, as described above.

Figure 4:
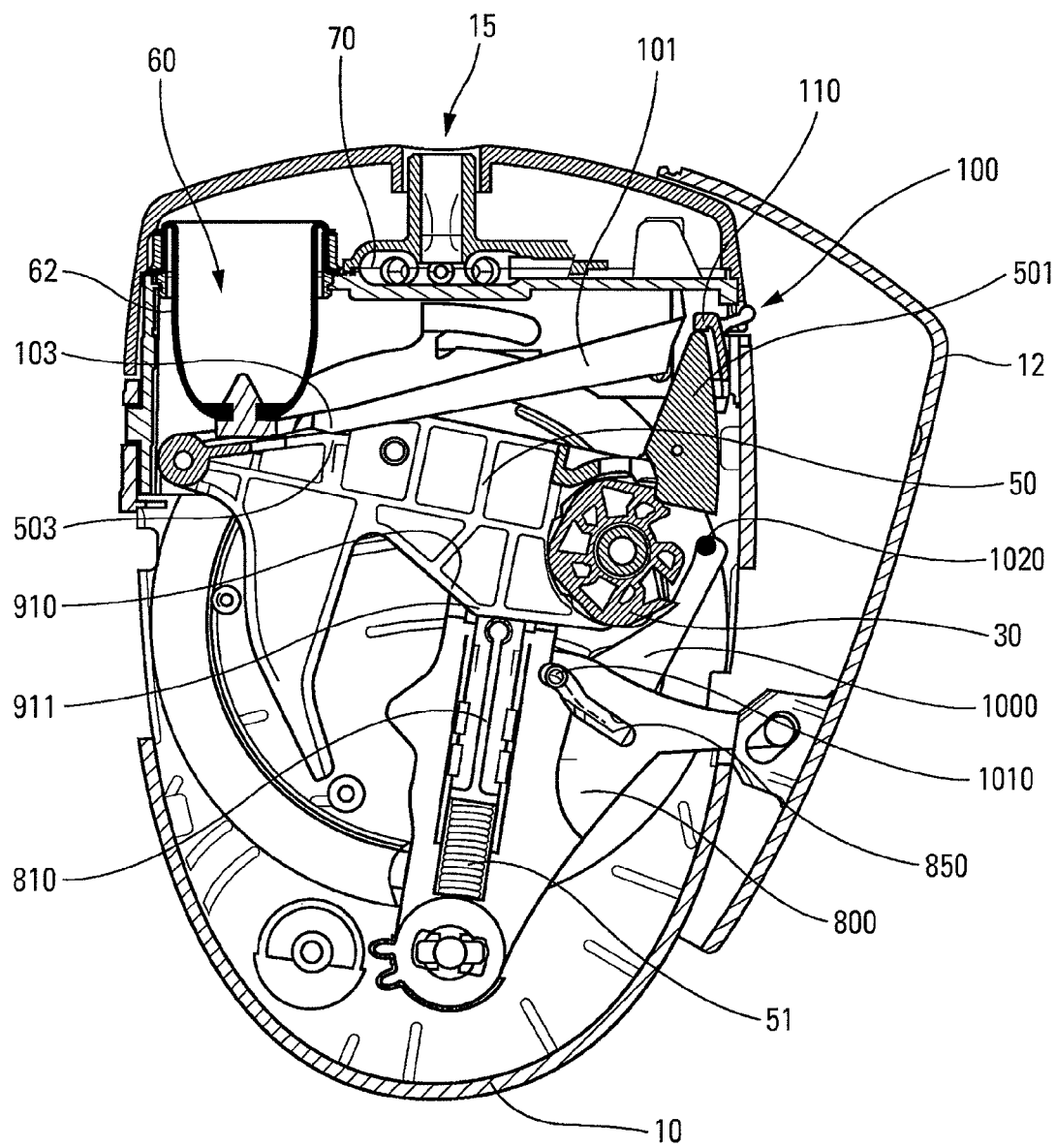
FIG. 4 is a view similar to the view in FIG. 3, shown in the open position.
Figure 6:
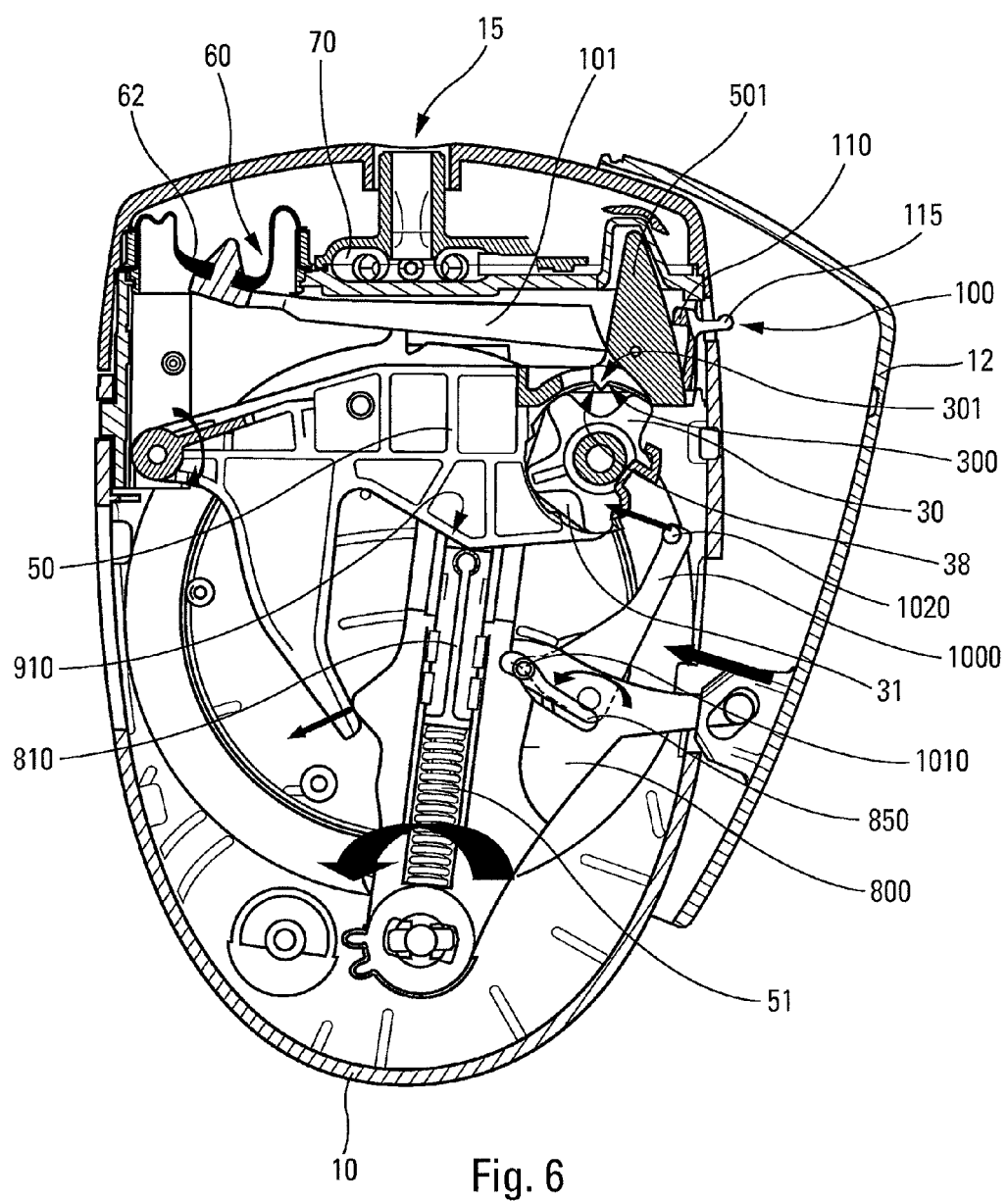
FIG. 6 is a view similar to the view in FIG. 5, shown at the start of closure, after inhalation.
Figure 7:
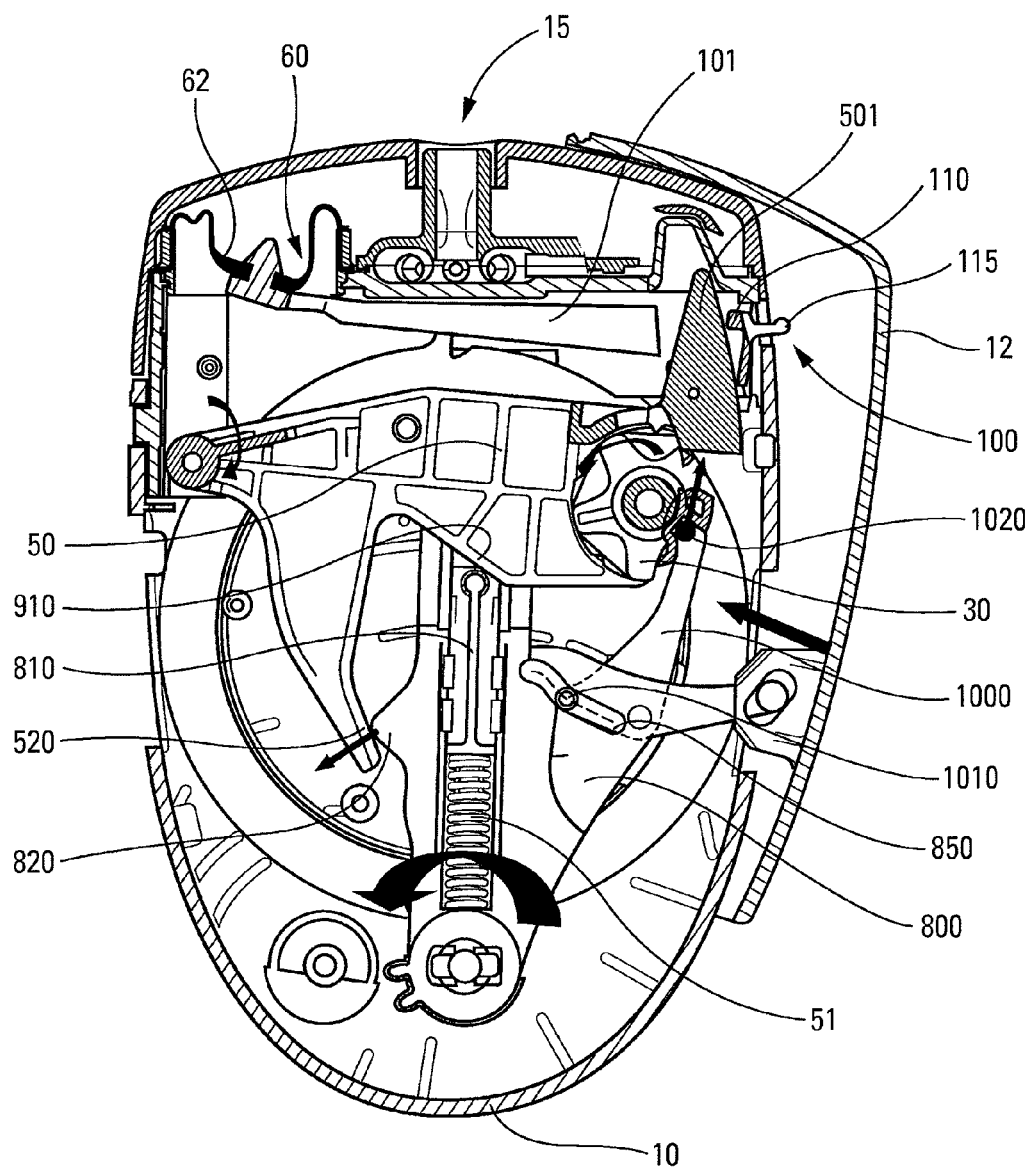
FIG. 7 is a view similar to the view in FIG. 6, shown during closure, after inhalation.
Figure 8:
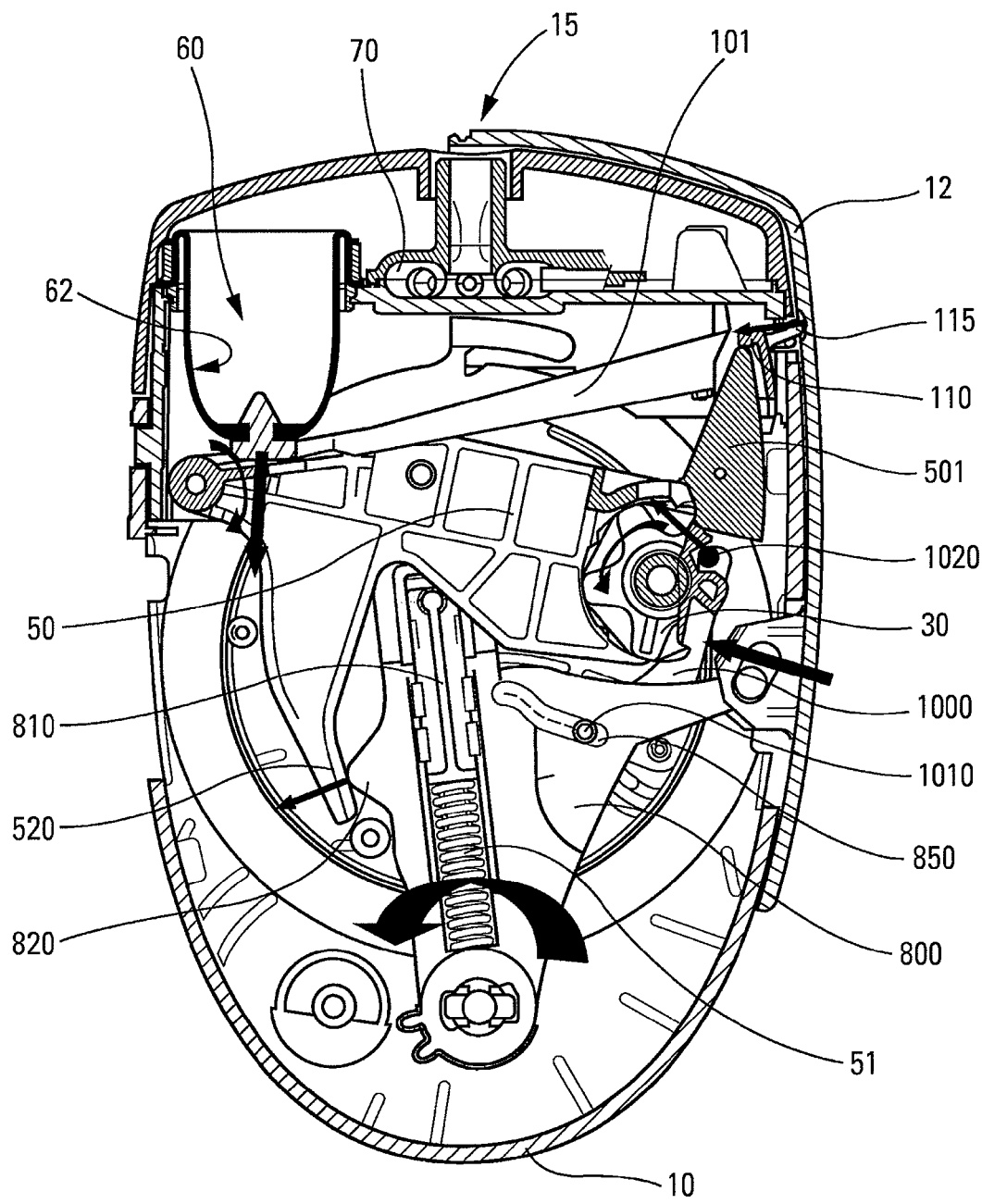
FIG. 8 is a view similar to the view in FIG. 7, shown once closed, after inhalation.
Figure 9:
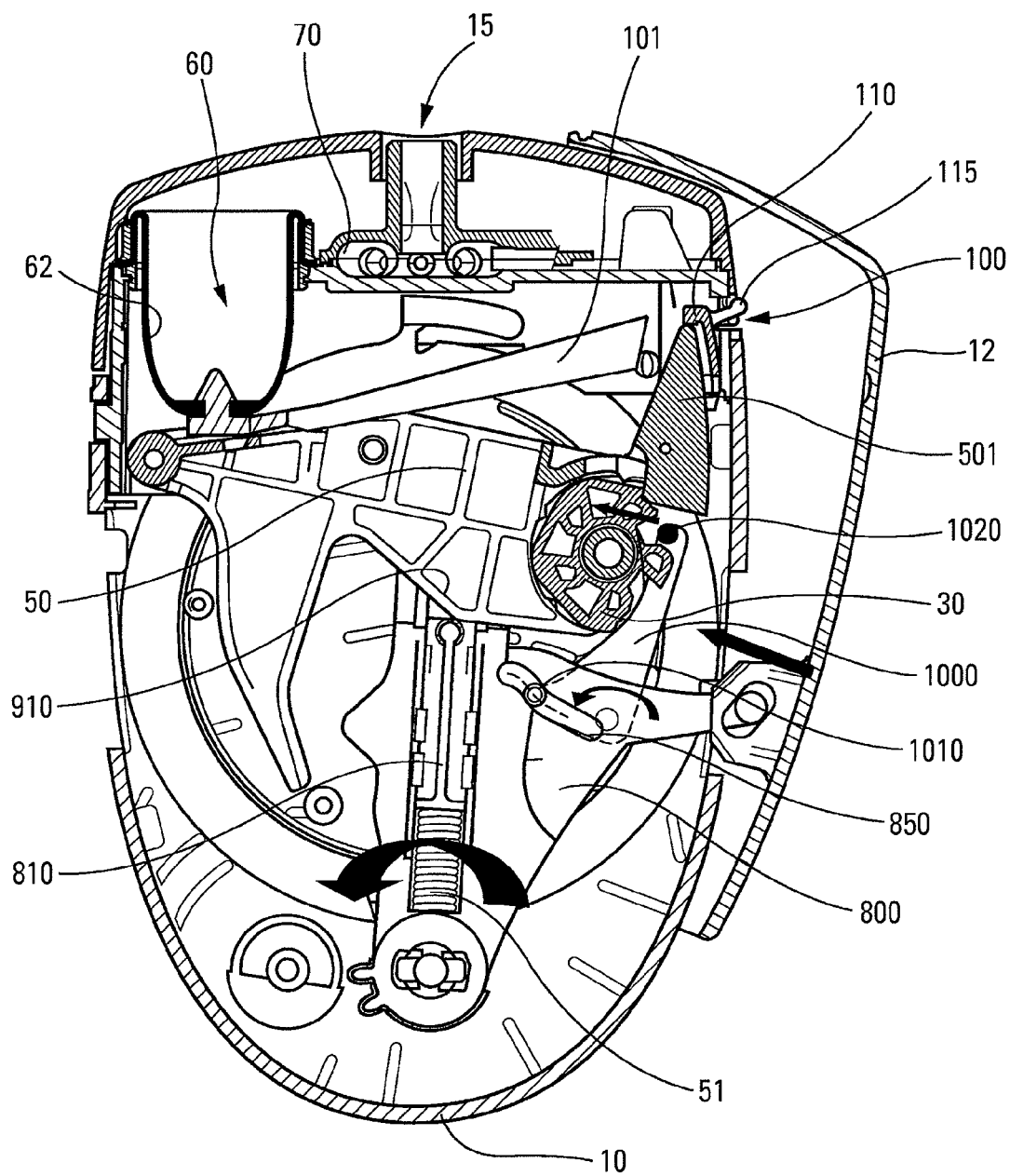
FIG. 9 is a view similar to the view in FIG. 4, shown at the start of closure, in the absence of any inhalation.
Figure 10:
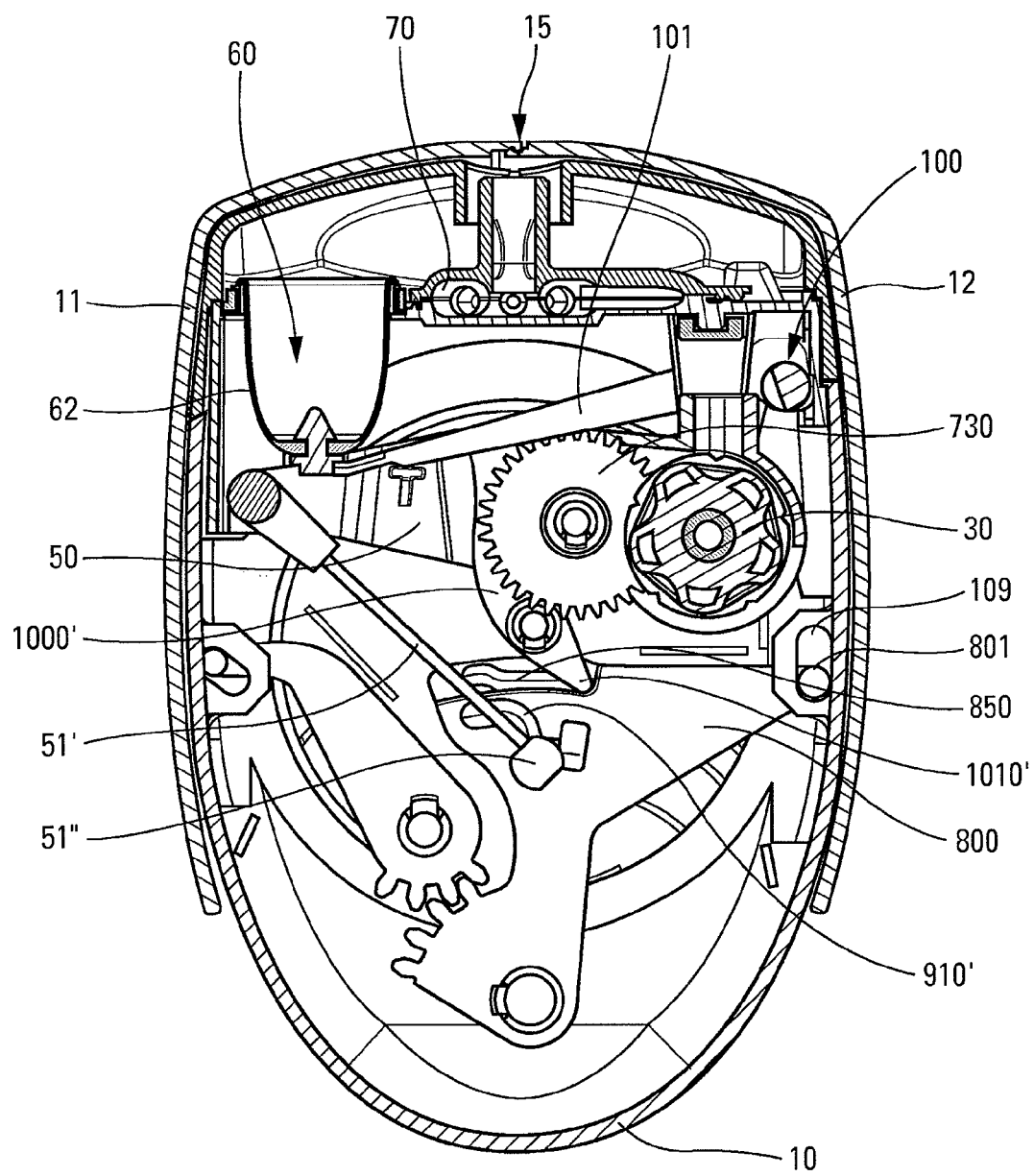
FIG. 10 is a diagrammatic section view of a device constituting another embodiment of the invention, shown in the closed position.

Advantageously, the drive element 1000 is pivotally mounted inside the body 10. As explained above, the drive element 1000 co-operates firstly with the groove 850 of the loading member 800 by means of its projection 1010. In addition, another projection 1020 of said drive element 1000 co-operates with a set of teeth 37 of the guide wheel 30. When the cover element 12 is in its closed position, the projection 1020 meshes with said set of teeth 37. When the cover element 12 is opened, the projection 1010 of the drive element slides in the groove 850 of the loading member causing said drive element 1000 to pivot about its pivot axis. Such pivoting causes the drive projection 1020 to disengage from said set of teeth 37 of the guide wheel 30. This disengaged position is shown in FIG. 4. When the user inhales, the movable support means 50 are displaced towards the dispensing position. Since the guide wheel 30 is fastened in rotary manner on said movable support means 50, obviously it is displaced together with said movable support means towards the opening means. In the dispensing position, the drive projection 1020 of the drive element 1000 is thus situated facing another tooth of the set of teeth 37 of the guide wheel 30, as clearly visible in FIG. 5. Then, when the user closes the cover element 12, the projection 1010 of the drive element once again slides in the groove 850 of the loading member 800, this time in the other direction, which in turn causes said drive element 1000 to pivot. The drive projection 1020 thus comes to mesh with another tooth, in particular the next tooth, of the set of teeth 37 of the guide wheel 30, as shown in FIGS. 6 to 8. Meshing advantageously occurs during the beginning, in particular in the first half, of the return stroke of the movable cover element 12 towards its closed position, and continuing the return stroke causes the guide wheel 30 to turn under the effect of said drive element 1000. In this way, the guide wheel 30 turns about its axis of rotation so as to bring the next full blister to face the opening means with a view to the next actuation of the device and thus the next dispensing of a dose. As explained above, the groove 850 of the loading member advantageously comprises two portions of different slopes. Starting from the closed position of the movable cover element, the first portion of the groove 850 advantageously does not cause the drive element 1000 to pivot, and it is only in the second portion of steeper slope in the groove 850 that the drive element 1000 is caused to pivot about its pivot axis so as to cause the drive element to disengage from the set of teeth 37. Consequently, when the user closes the cover, the drive projection 1020 of the drive element 1000 returns quickly inside the next tooth of the set of teeth 37, and continuing the return stroke of the movable cover element towards its closed position causes said guide wheel 30 to turn.

The cam surface 910 also includes at least two portions of different slopes that are advantageously separated by a vertex 911. Starting once again from the closed position of the movable cover element, the first slope portion on which the rod 810 slides, enables the spring 51 to be compressed, as describe above. When the spring is loaded, i.e. compressed, the cam surface 910 provides a second different slope portion with which the rod 810 co-operates when the device is in its open position. The rod 810 preferably exerts a force that is substantially perpendicular on the second cam surface portion, as shown in FIG. 4. In this way, the loaded position is stable.

In the open position, shown in FIG. 4, the movable support means 50 that are urged towards the dispensing position by the compressed spring 51 thus exert a force on the blocking means 100, in particular on the blocking element 110 of the blocking means, by means of the extension 501. At the opposite end of the rod 101, in the proximity of the connection of said rod 101 to the diaphragm 62, a bearing zone 103 is advantageously provided, adapted to co-operate with a complementary zone 503 provided on the movable support means 50. The bearing zone 103 makes it possible to create a loaded position that is stable between said movable support means 50 and said blocking means 100. Each of the two means are movable, and the dual contact, firstly with a force exerted upwards (with reference to the position shown in FIG. 4) by the extension 501 on the shoulder portion 110, and secondly with a force exerted downwards by the bearing zone 103 on the complementary zone 503, guarantees balanced blocking that can be released only by the user inhaling, causing the diaphragm 62 to deform, and thus the rod 101 of the blocking means 100 to pivot.

After inhalation, i.e. in the dispensing position shown in FIG. 5, the blocking means 100 have pivoted, and the movable support means 50 have been displaced upwards by the compressed spring 51. The pivoting of the blocking means, in particular of the blocking element 110, causes an end portion 115 of the blocking element 110 to project out from the body 10, as shown in particular in FIG. 5. Then, when the user closes the movable cover element 12, said cover element 12, when fully closed, comes to bear against said end portion 115, thereby returning the blocking means 100 to their initial position with the diaphragm 62 that is also returned to its initial position, as shown in particular in FIG. 8.

Thus, by opening the inhaler, the user loads the system. If the user does not inhale and closes the inhaler, said inhaler merely returns to its start position without displacing the reservoirs 21 or the blocking means 100. There is thus no risk of a reservoir (and thus an active dose of substance) being lost by accidental or incomplete actuation in which the user does not inhale between opening and closing. Opening the reservoir, emptying it, dispensing the powder into the lungs of the user, and displacing the blister strip to bring a new full reservoir to face the opening means is thus possible only if the user inhales.

In addition, after inhalation and thus displacement of the movable support means 50 towards the dispensing position, closure of the movable cover element 12 returns the loading member 800 towards its start position. As shown in FIG. 6, it is at this moment that the projection 820 of the loading member 800 co-operates with the extension portion 520 of the movable support means 50 so as to push said movable support means 50 and thus cause them to pivot towards their non-dispensing position. The movable support means 50 are thus advantageously returned towards the non-dispensing position that is mechanically linked to the closure of the movable cover element 12.

As explained above, FIGS. 2 to 9 show only one movable cover element 12, but naturally a second movable cover element, advantageously symmetrical to the movable cover element shown, could be provided around the body 10, as shown in FIG. 1. Advantageously, the two movable cover elements 11, 12 are then meshed together so as to guarantee symmetrical opening and closing of said two movable cover elements. They can be meshed together in the proximity of their pivot point.

Figure 22:
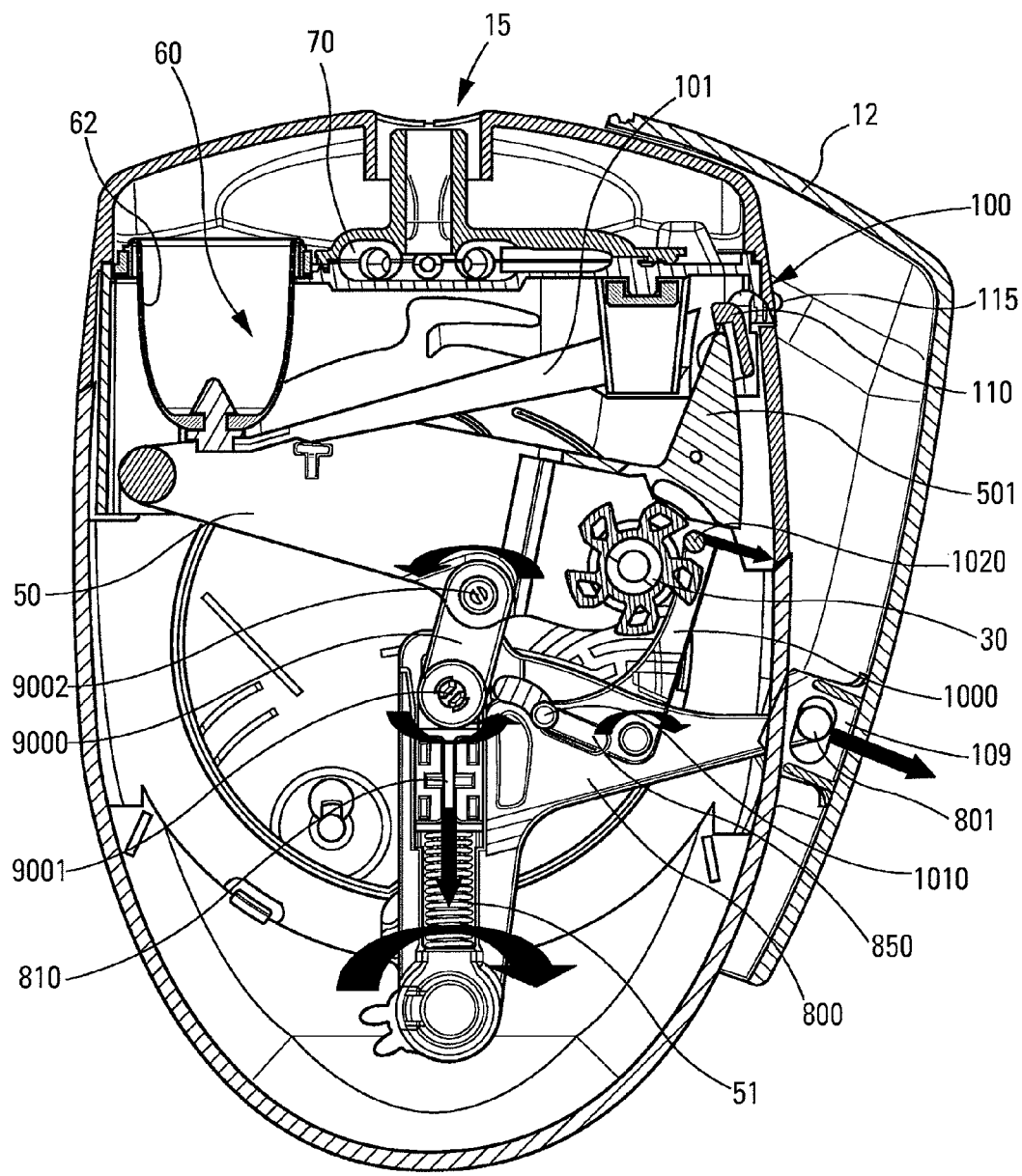
FIG. 22 is a view similar to the view in FIG. 21, shown during opening.
Figure 23:
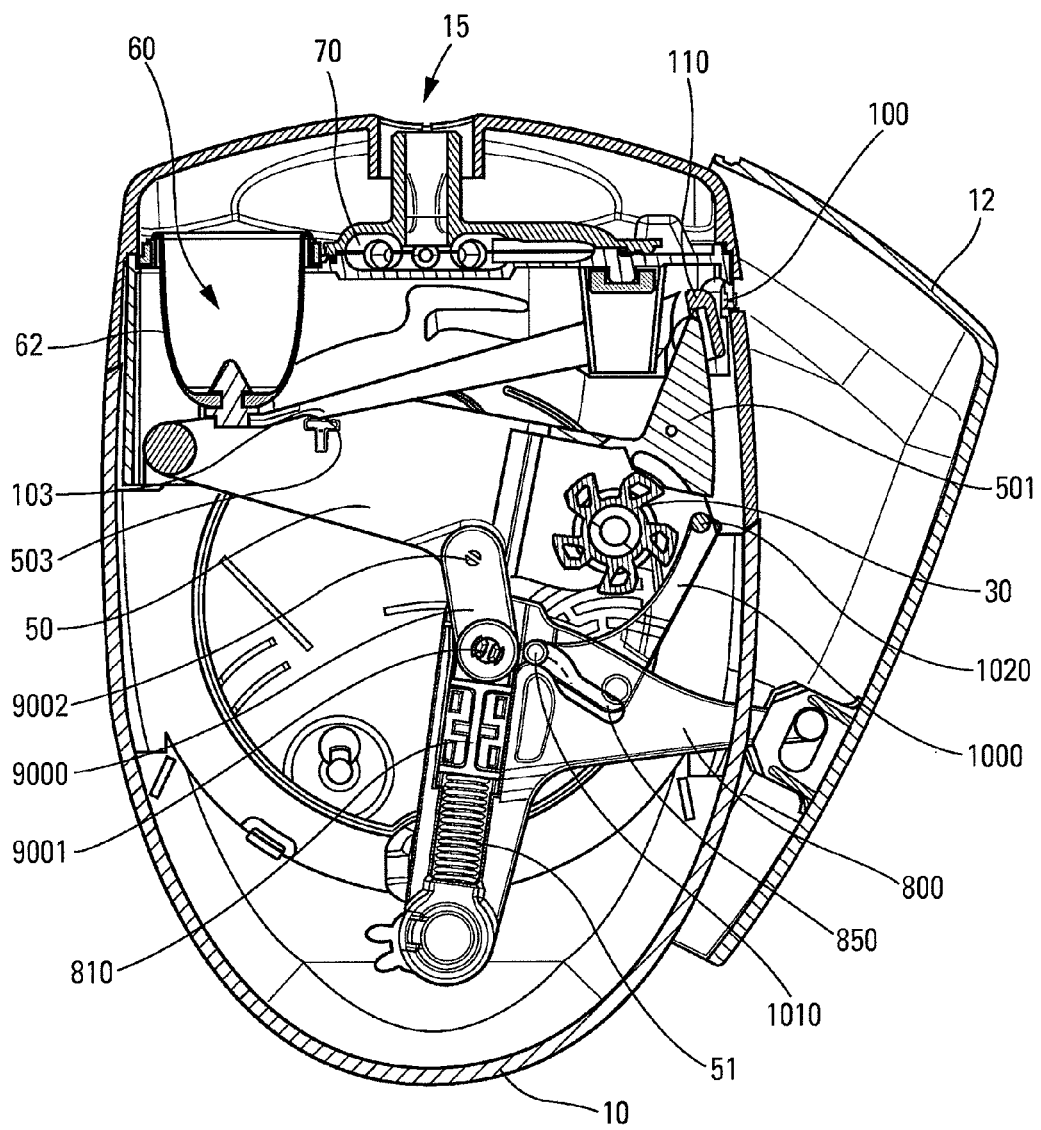
FIG. 23 is a view similar to the view in FIG. 22, shown in the open position.
Figure 24:
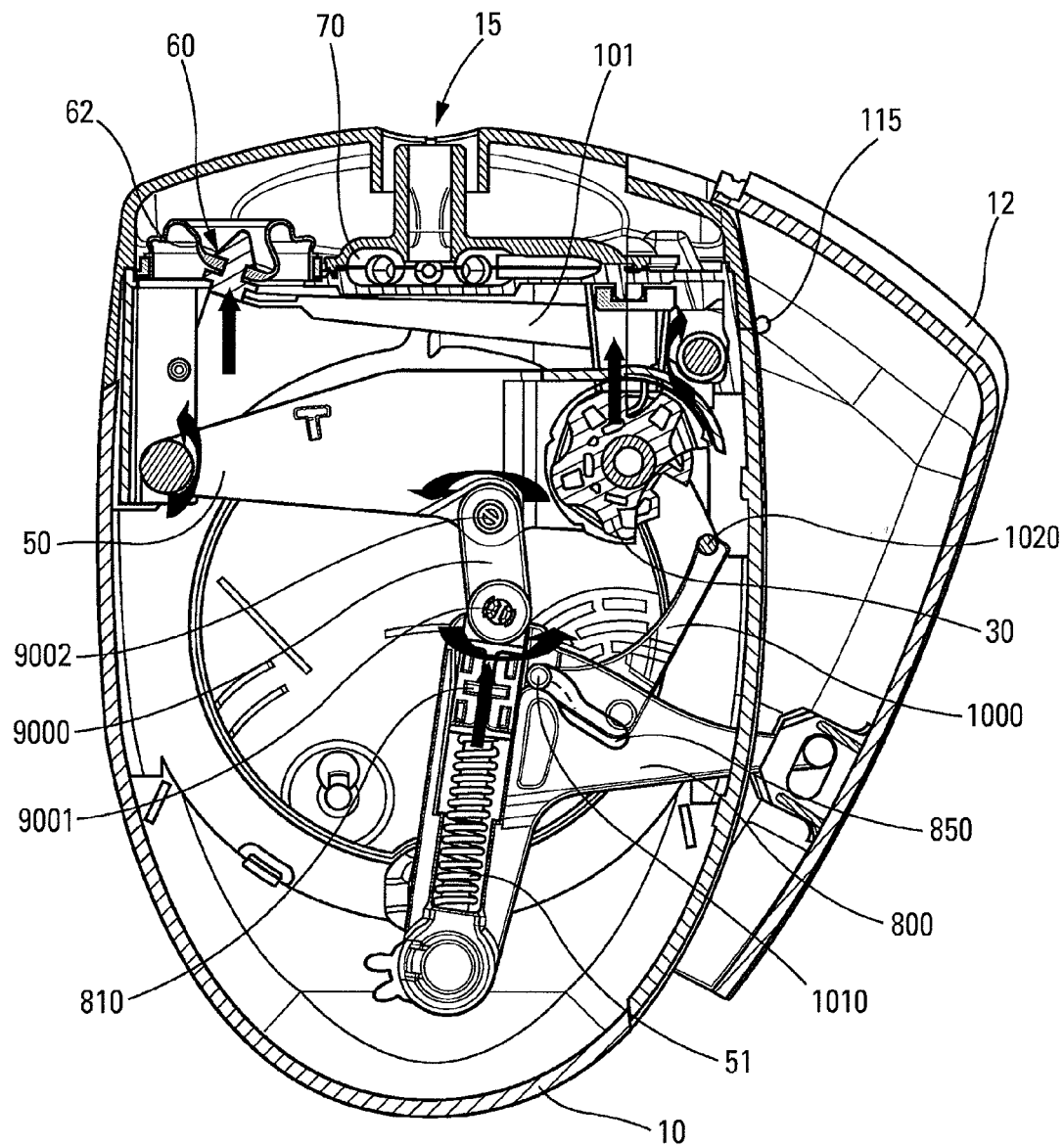
FIG. 24 is a view similar to the view in FIG. 23, shown after inhalation.
Figure 25:
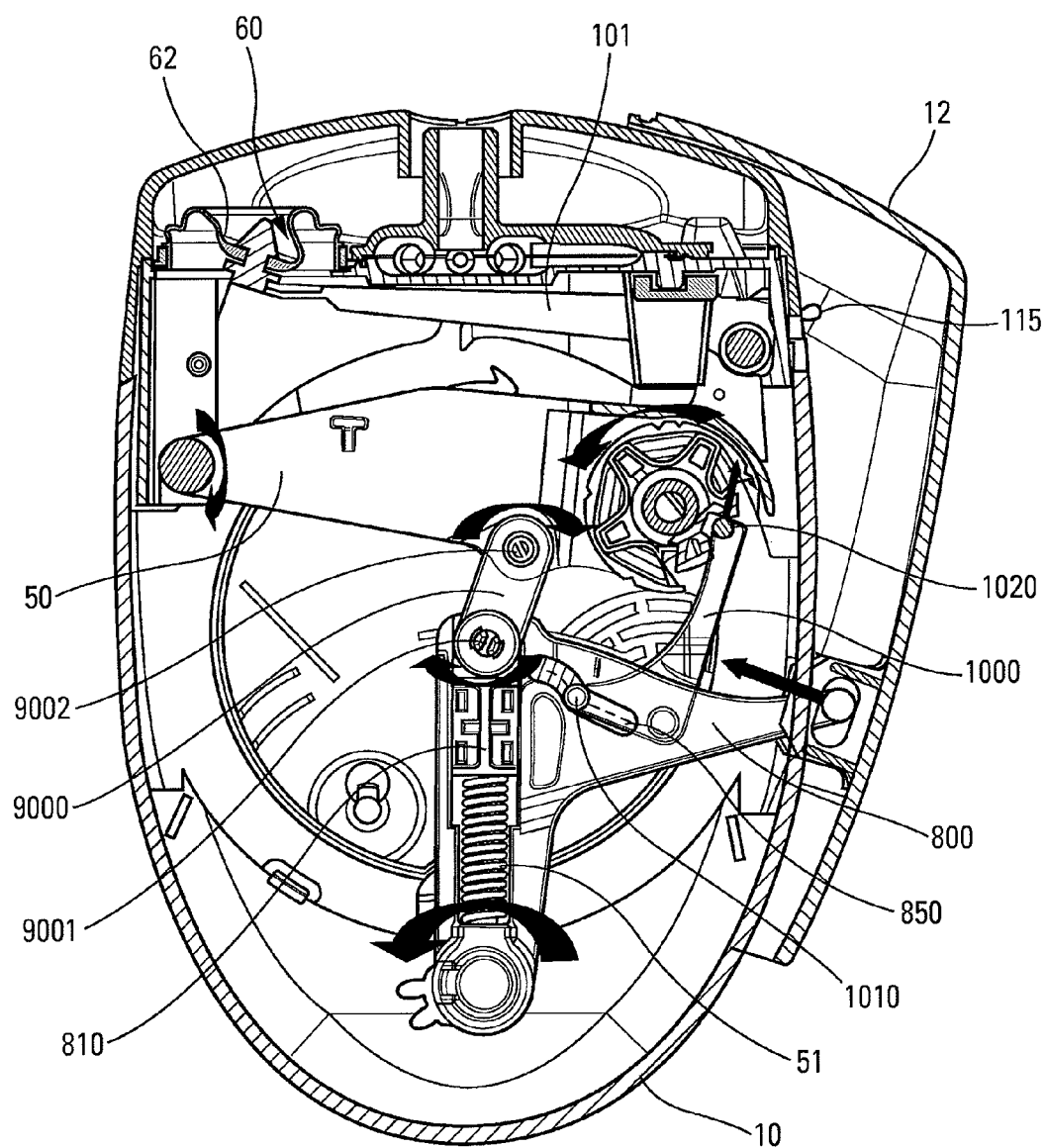
FIG. 25 is a view similar to the view in FIG. 24, shown during closing, after inhalation.
Figure 26:
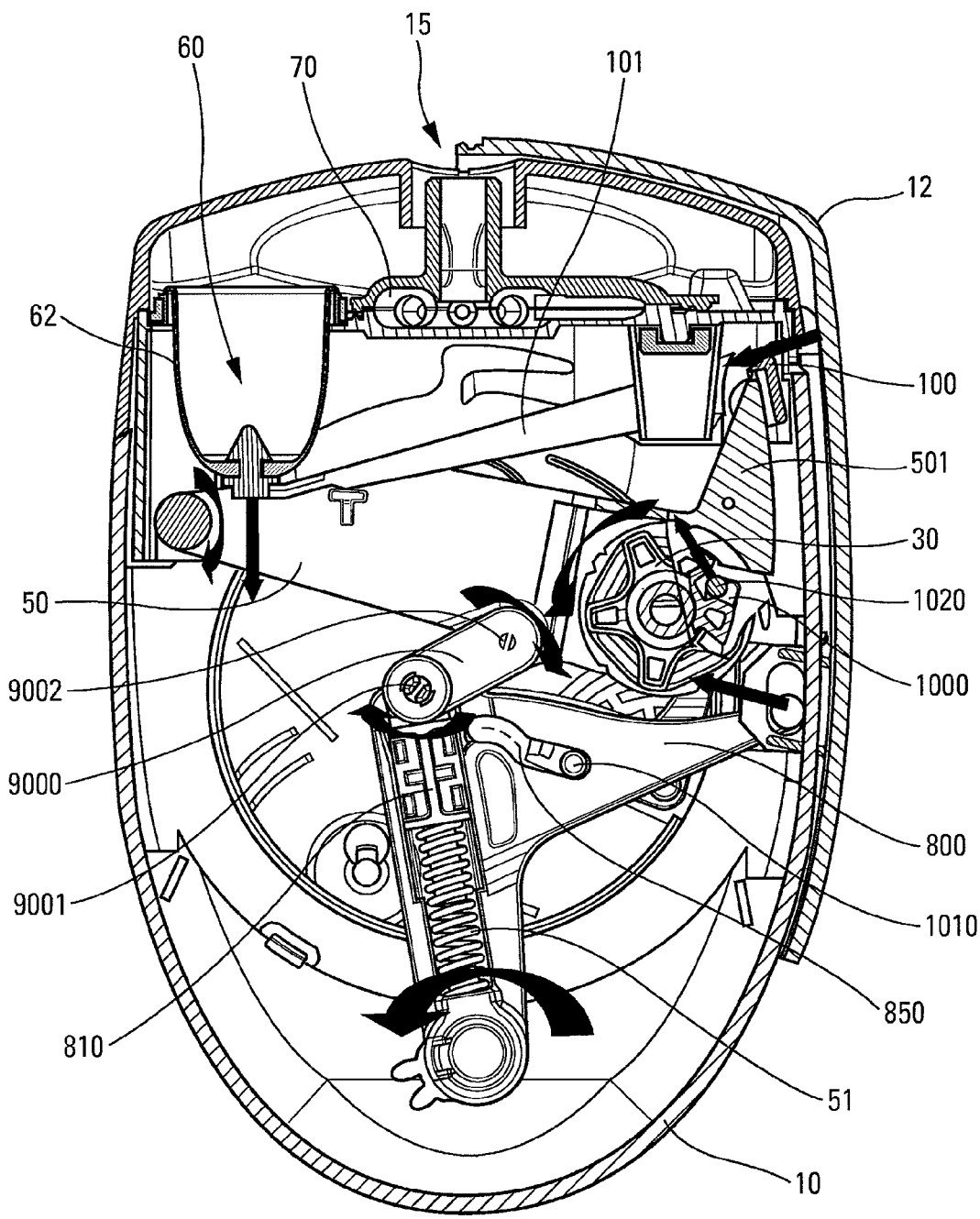
FIG. 26 is a view similar to the view in FIG. 25, shown once closed, after inhalation.
Figure 27A:
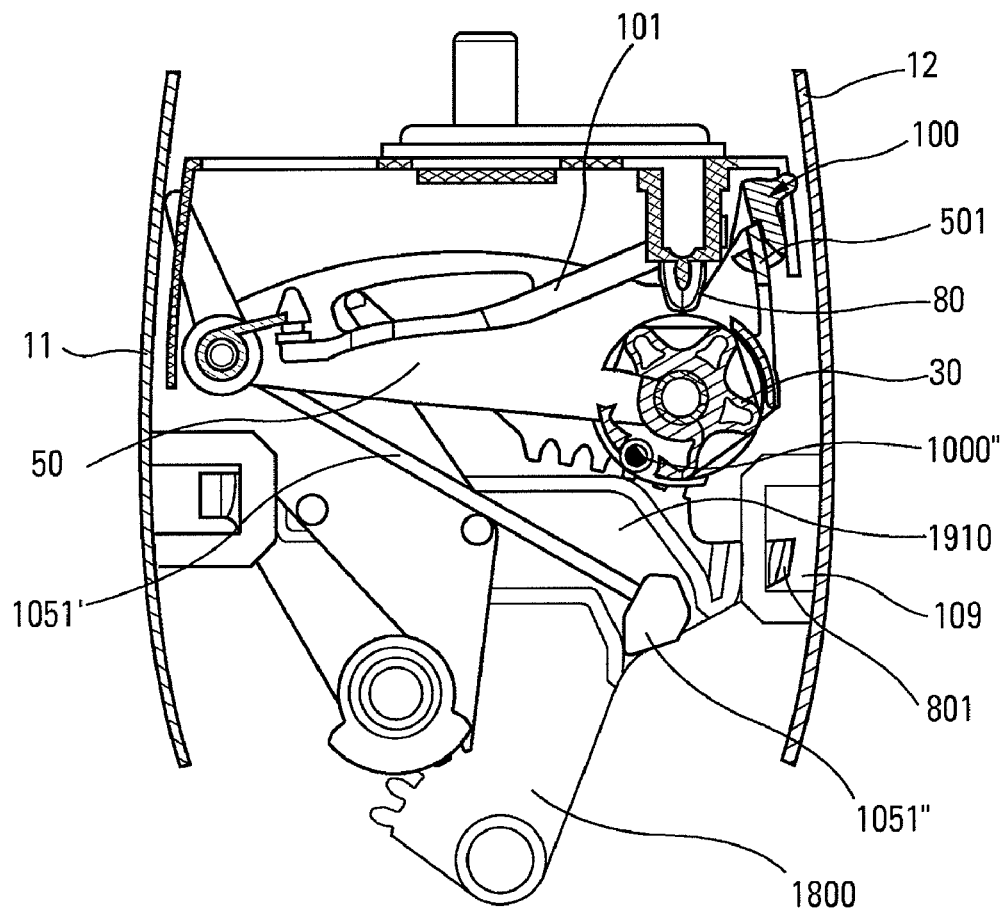
FIGS. 27a and 27b are diagrammatic section views, respectively from the front and from the rear, of another embodiment of the invention, shown in the closed position.
Figure 27B:
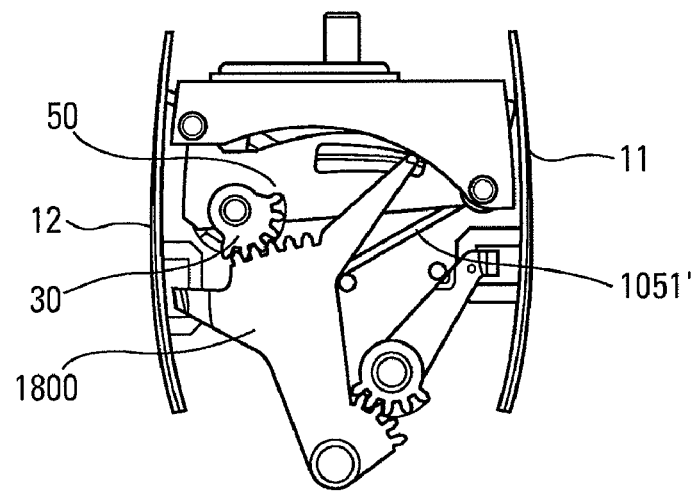
Figure 28A:
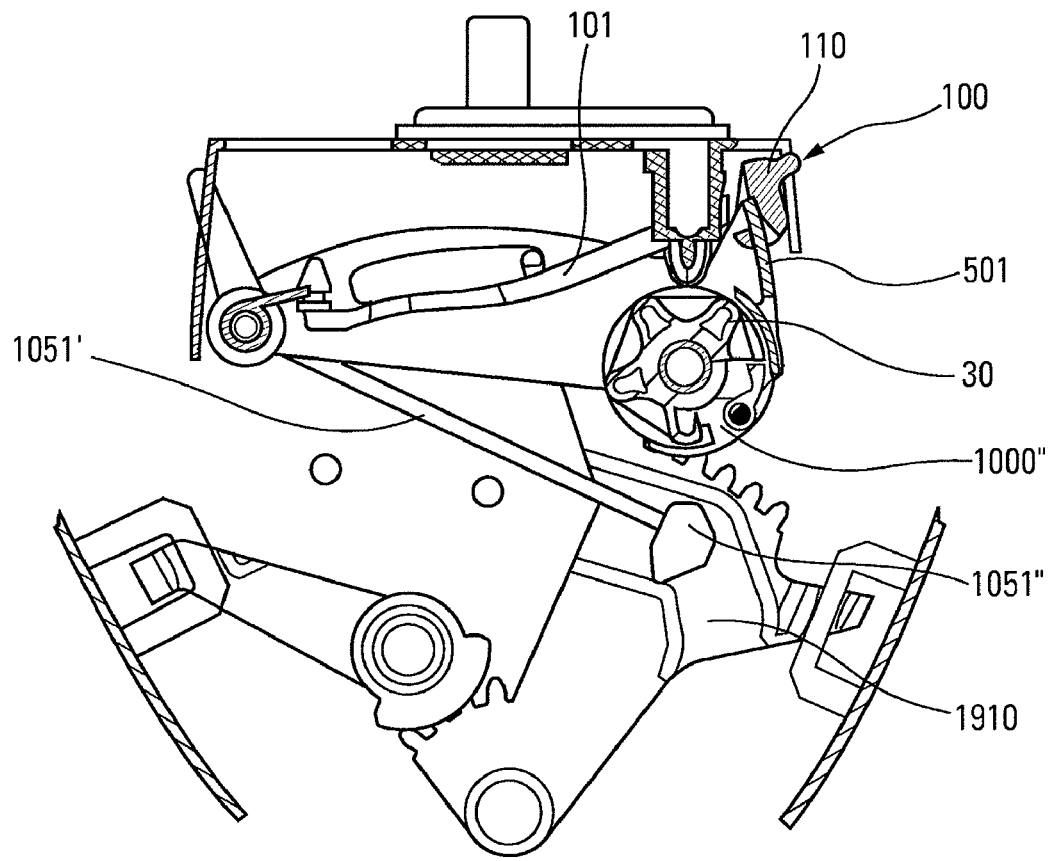
FIGS. 28a and 28b are views similar to the views in FIGS. 27a and 27b, shown in the open position.
Figure 28B:
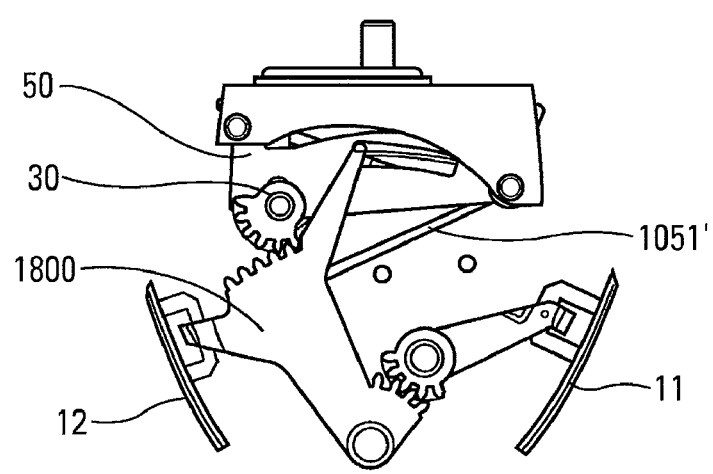
Figure 29A:
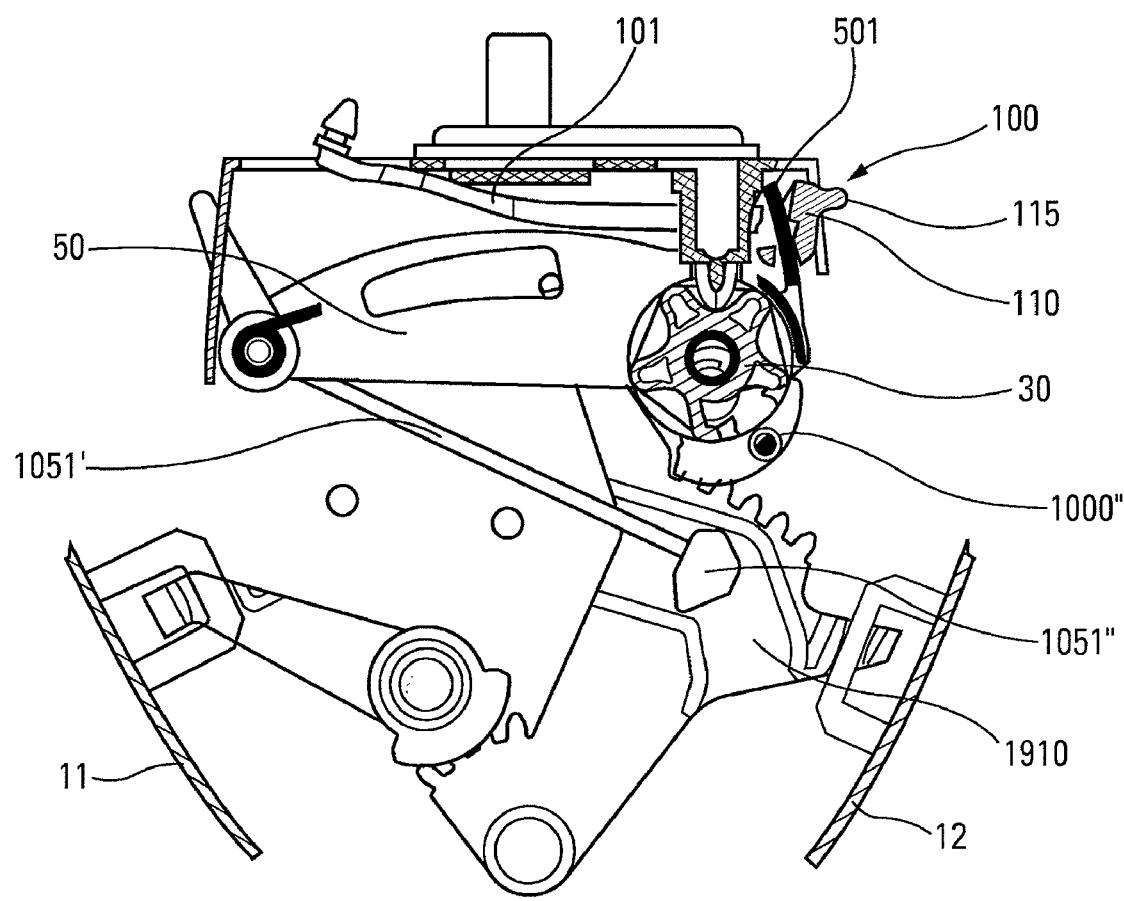
FIGS. 29a and 29b are views similar to the views in FIGS. 28a and 28b, shown after inhalation.
Figure 29B:
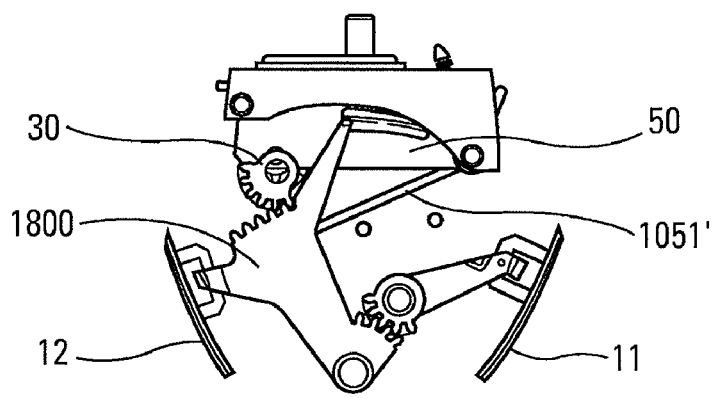
Figure 30A:
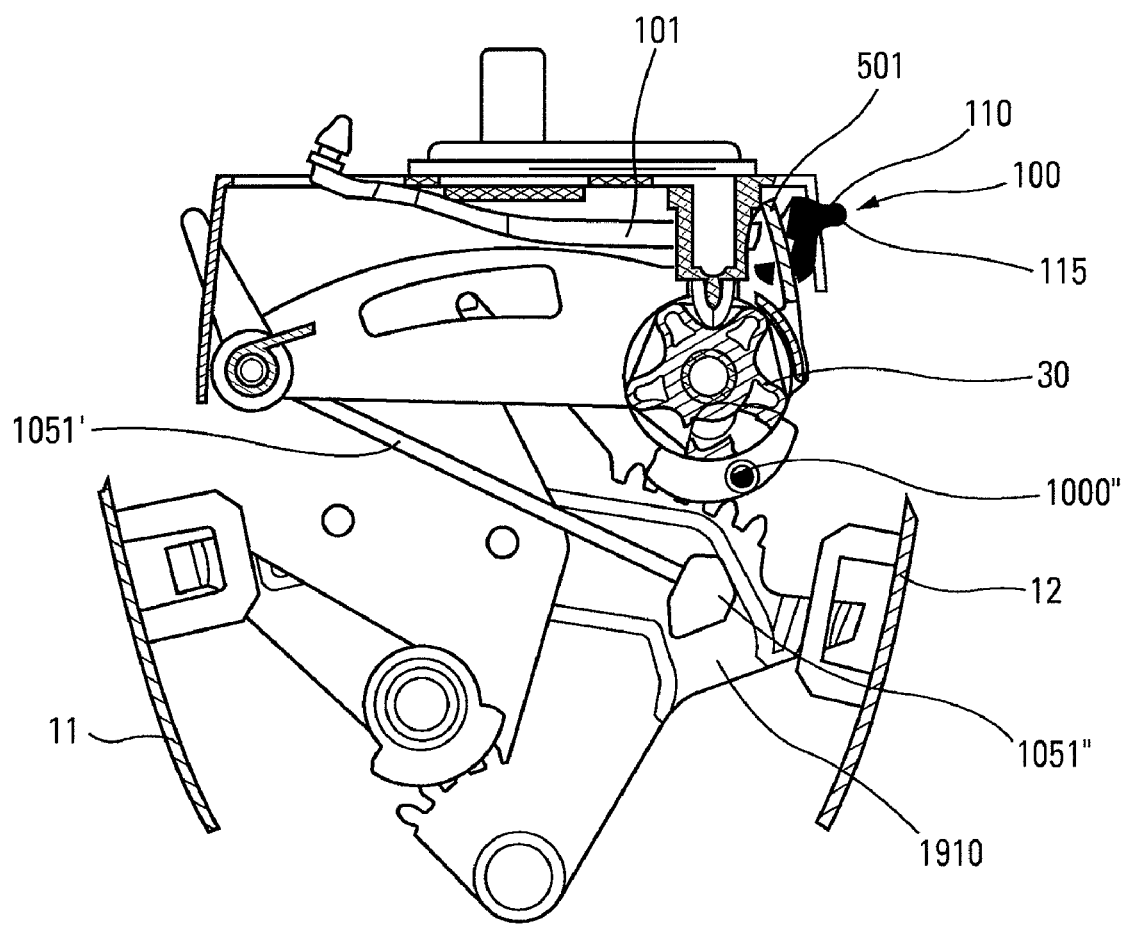
FIGS. 30a and 30b are views similar to the views in FIGS. 29a and 29b, shown during closure, after inhalation.
Figure 30B:
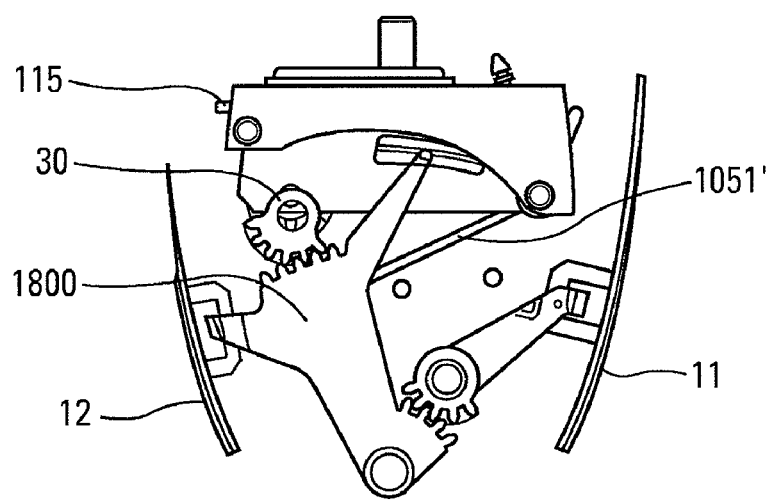
Figure 31A:
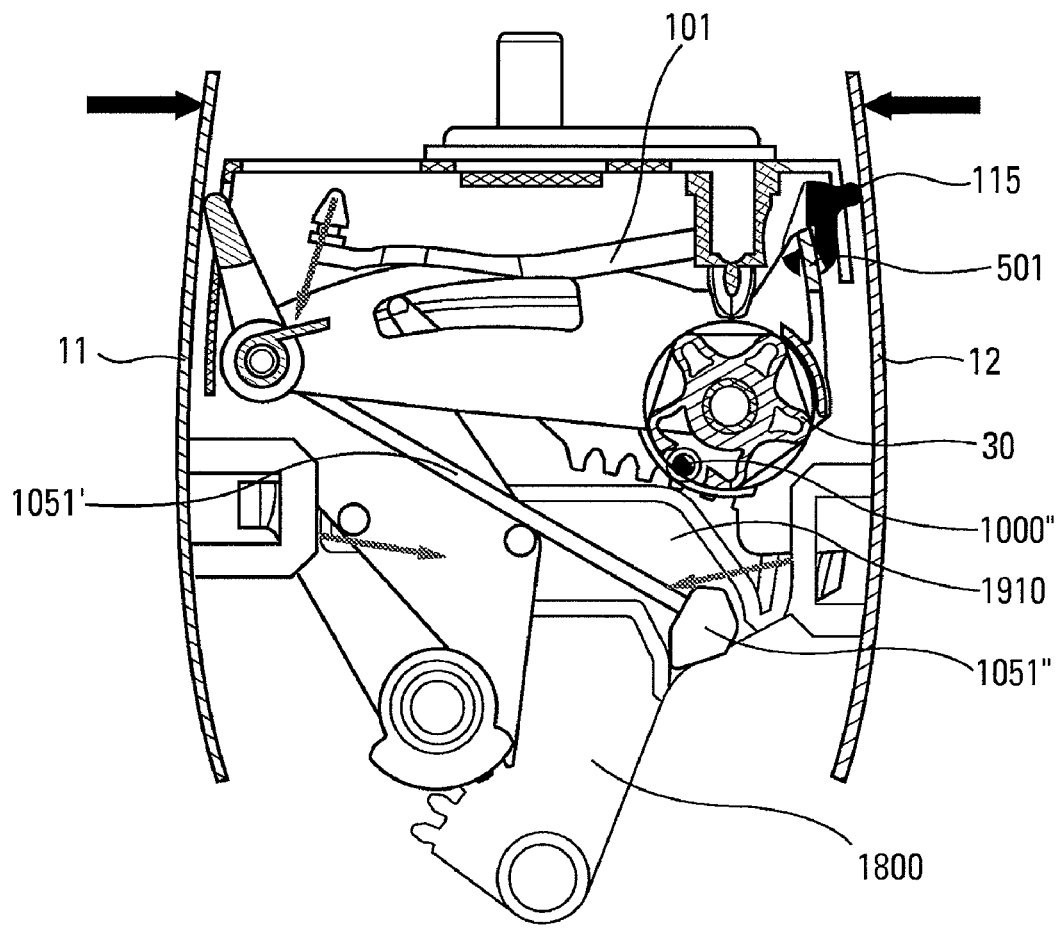
FIGS. 31a and 31b are views similar to the views in FIGS. 30a and 30b, shown once closed, after inhalation.
Figure 31B:
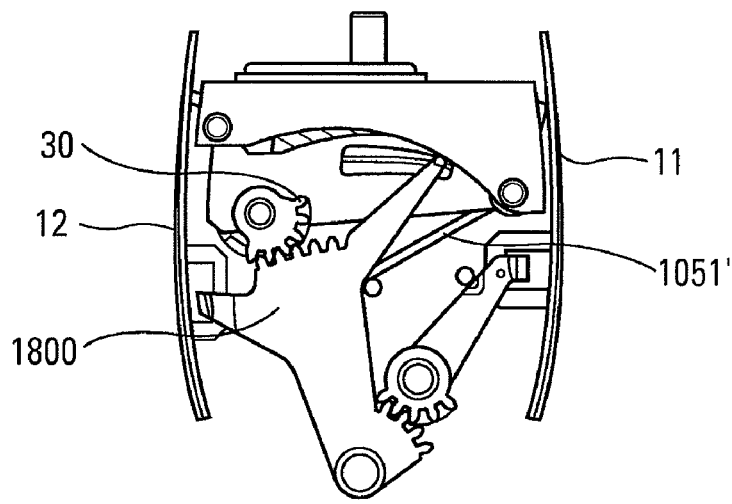

FIGS. 21 to 26 show a variant embodiment in which the cam surface 910 is replaced by a connecting rod or toggle 9000 that is pivotally connected firstly to the rod 810 that is connected to the spring 51 and secondly to the movable support means 50, by means of two respective pivot axes 9001 and 9002. In the closed position, shown in FIG. 21, the toggle 9000 forms an angle relative to the rod 810 and the longitudinal axis of the spring 51. When the user opens the cover elements 11, 12, the user pulls on the axis 9001, displacing the loading member 800 towards the right in the figure, as shown by the arrows in FIG. 22. Since the movable support means 50 are stationary as a result of being retained by the blocking means 100, the toggle thus becomes straight so as to align itself with the axis of the rod 810 and of the spring 51, as shown in FIG. 22. This causes the spring 51 to compress as a result of the toggle being longer than it is wide. In the open position shown in FIG. 23, the toggle advantageously extends beyond the longitudinal axis of the rod 810 and of the spring 51, so as to guarantee an open position that is stable. As above, if the user closes the inhaler without inhaling, nothing happens at the blister strip, which has not moved. After inhalation (FIG. 24), the blocking means are released, as described above, a reservoir is opened, and a dose is expelled. Then, when the user closes the cover elements 11, 12 (FIGS. 25 and 26), the toggle 9000 pivots back towards its initial position, thereby returning the movable support means 50 into their non-dispensing position. The blocking means 100 and the connection means 1000 are substantially identical to those in the embodiment in FIGS. 2 to 9, but variants can also be envisaged.

FIGS. 10 to 14 show another embodiment of the invention. In this embodiment, the identical or similar elements are represented by identical numerical references, whereas the elements that differ are represented by numerical references including primes.

Figure 11:
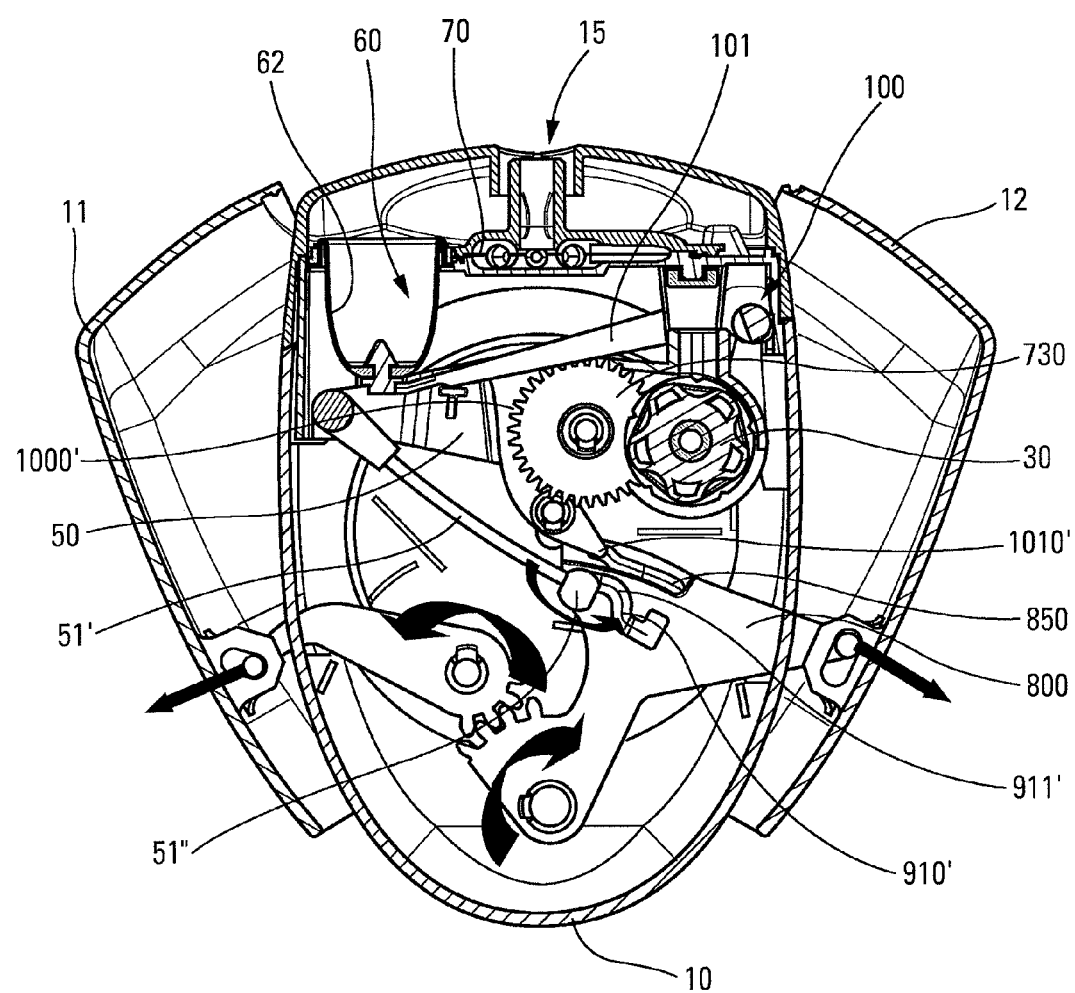
FIG. 11 is a view similar to the view in FIG. 10, shown in the open position.
Figure 12:
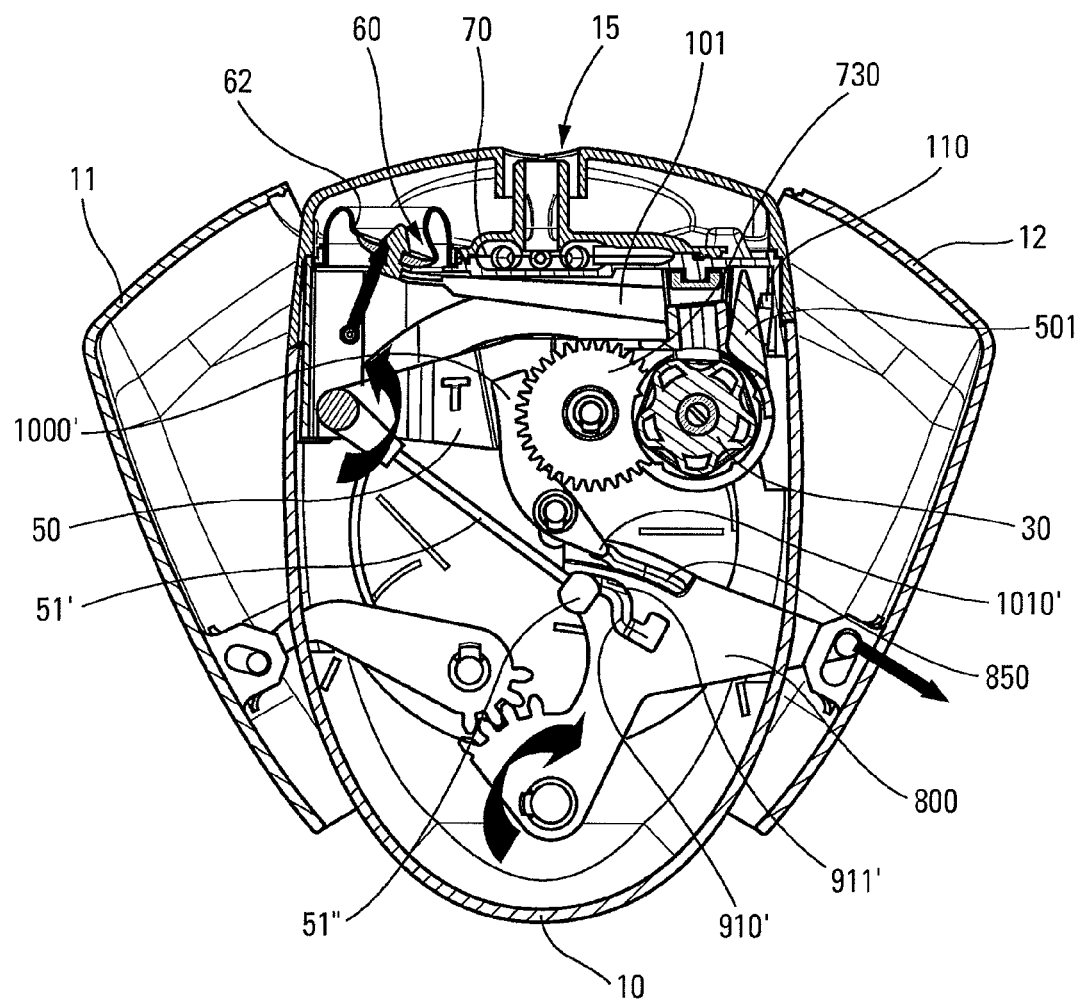
FIG. 12 is a view similar to the view in FIG. 11, shown after inhalation.
Figure 13:
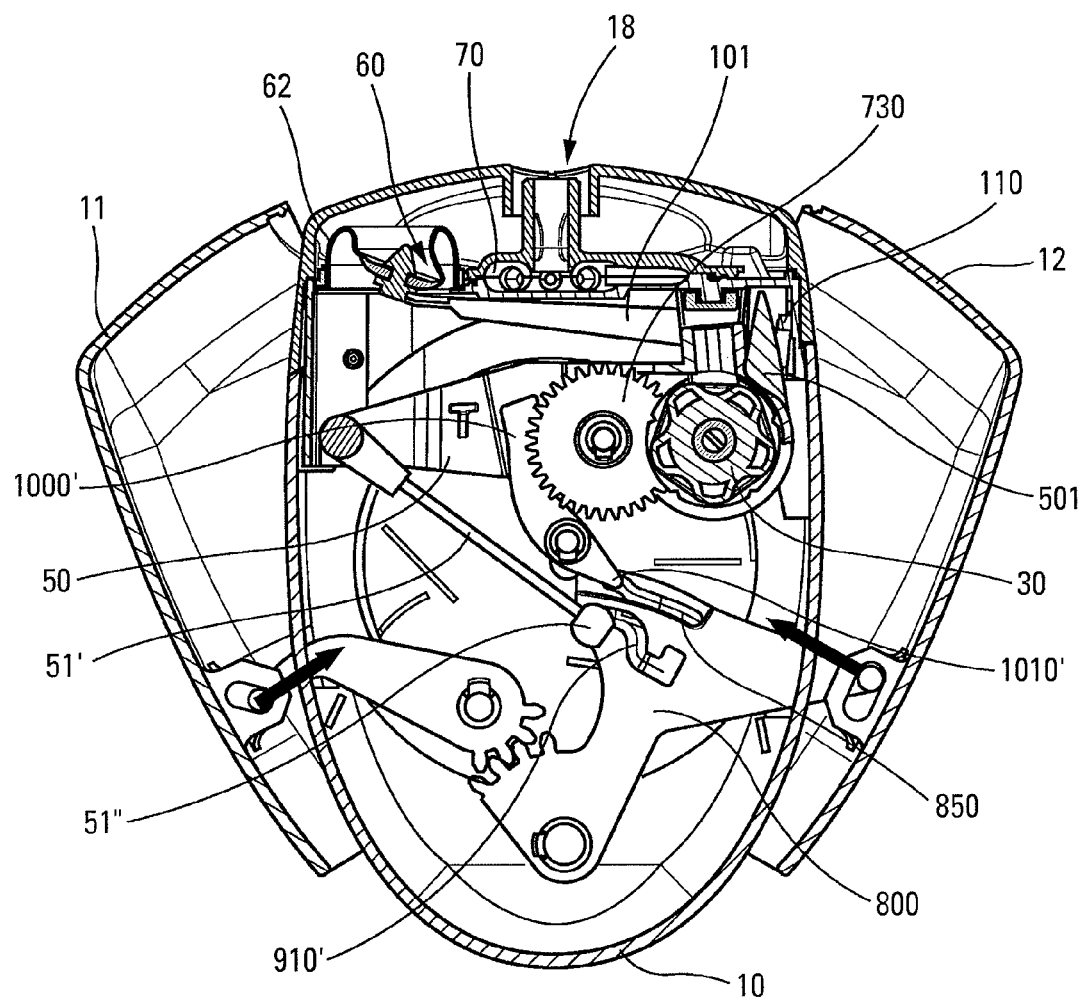
FIG. 13 is a view similar to the view in FIG. 12, shown during closure, after inhalation.
Figure 14:
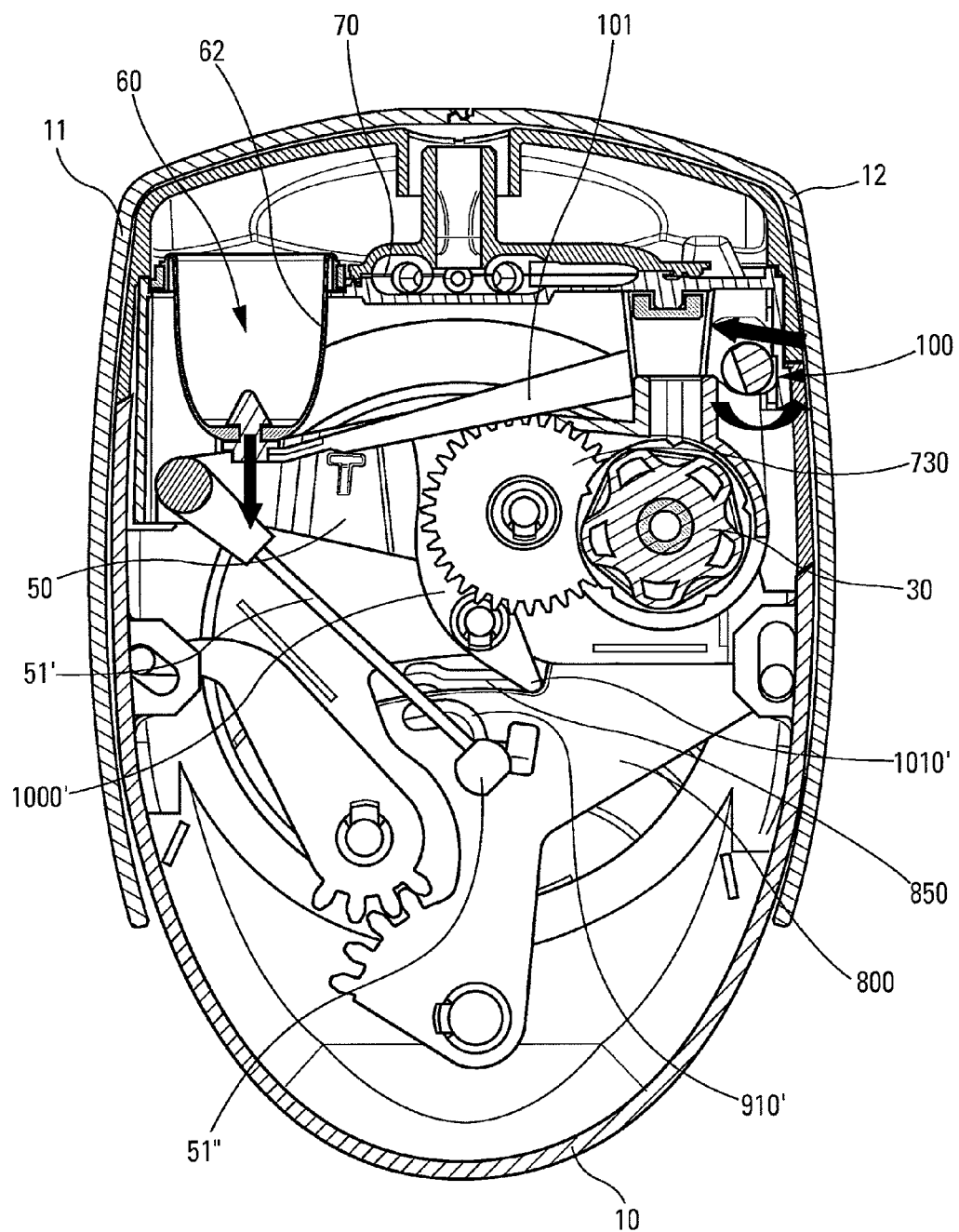
FIG. 14 is a view similar to the view in FIG. 13, shown once closed, after inhalation.
Figure 15:
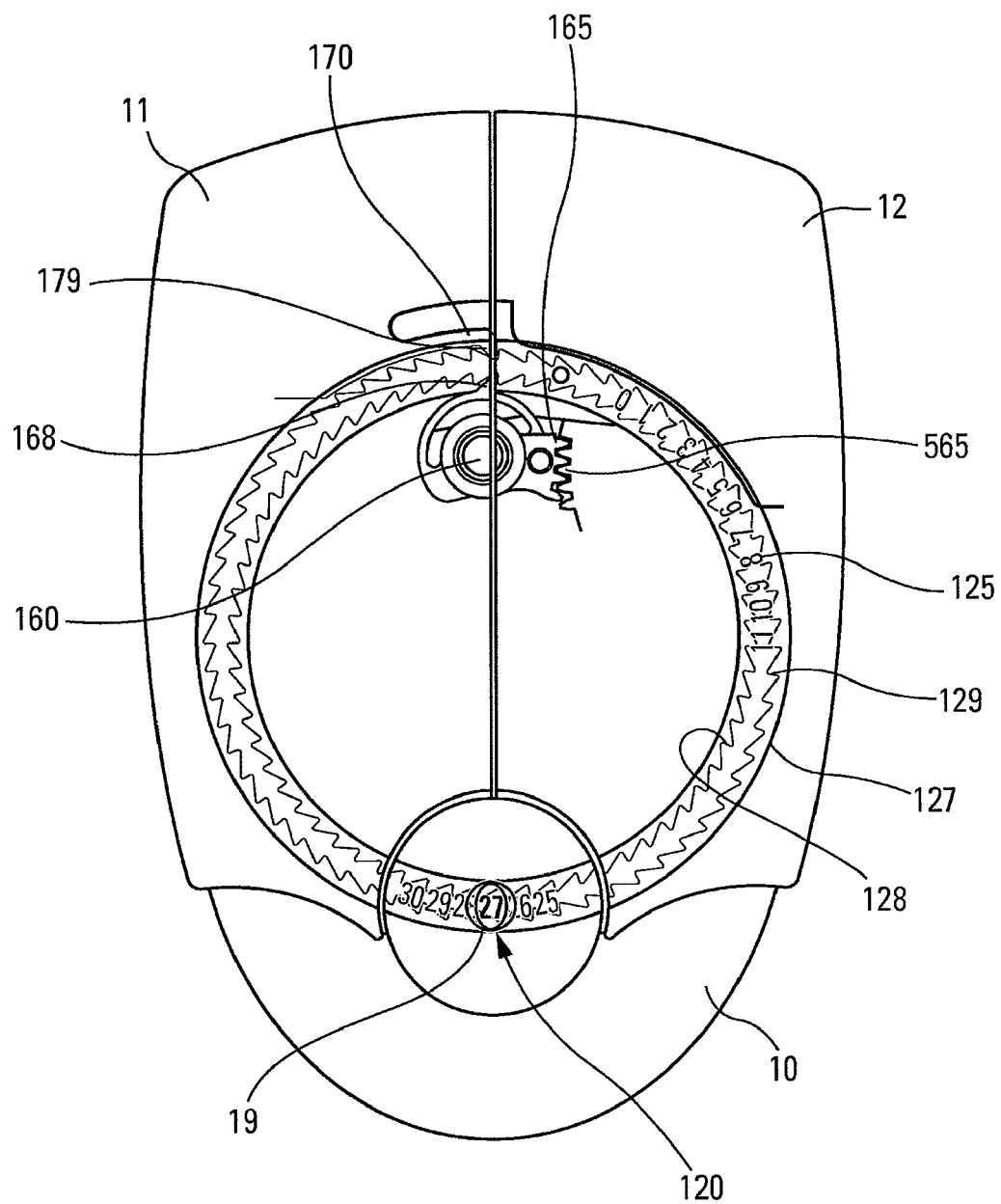
FIG. 15 is a diagrammatic view of a device constituting a variant embodiment of the invention, showing in transparency the metered dose inhaler in the closed position.
Figure 16:
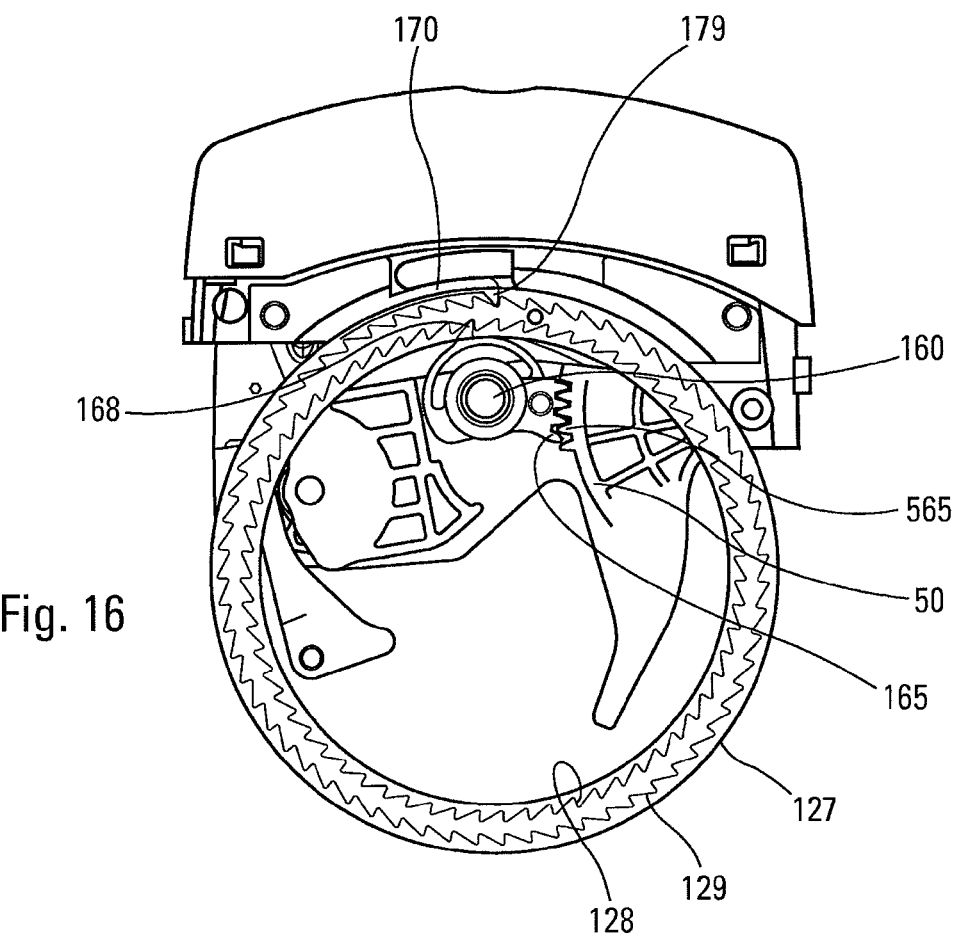
FIG. 16 is a diagrammatic section view of the FIG. 15 device.
Figure 17:
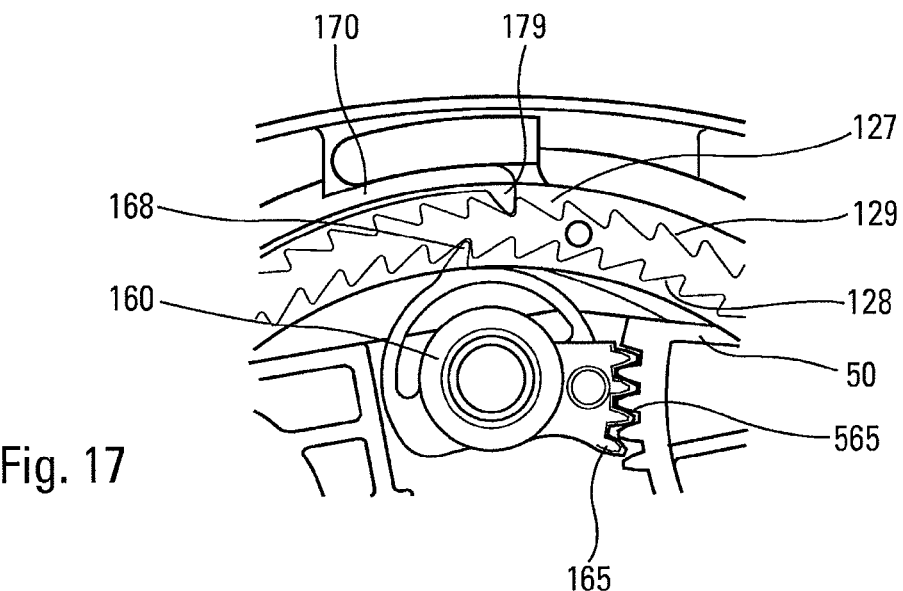
FIG. 17 is view of a detail in FIG. 16.

The embodiment differs from the above mainly by the loading means that are made in another way. In this second embodiment, there is no longer a spring 51 but a rod 51' that can flex so as to exert the resilient force on the movable support means. The rod 51' is thus firstly fastened to the movable support means 50, and secondly it is connected to the cocking member 800, advantageously by means of a projection 51" that penetrates into a groove 910' of appropriate shape. The groove forms a cam surface 910' against which said projection 51" of the rod 51' comes to slide during opening and closing of the movable cover elements 11, 12. The shape of the groove, approximately in the shape of a circular arc, thus comprises a first groove portion and a second groove portion that are connected at a vertex 911'. As for the cam surface 910 of the first embodiment in FIGS. 2 to 9, the first portion of the groove 910' serves to load the spring, i.e. the resilient rod 51', by deforming it, whereas the second portion of the groove 910' makes it possible to provide a position that is stable in the loaded position, i.e. in the open position. When the device is loaded, as shown in FIG. 11, the flexed flexible rod 51' thus exerts a force on the movable support means 50, so as to urge them towards their dispensing position. In manner similar to the first embodiment in FIGS. 2 to 9, the movable support means 50 are held in the non-dispensing position by the blocking means 100 that can be made in manner very similar to the manner described above. When the user inhales, the blocking means 100 are released and the movable support means 50 can be displaced towards their dispensing position towards the opening means.

Another difference in this embodiment relates to the displacement means for displacing the reservoir substrate, in particular the blister strip. In this second embodiment, the guide wheel 30 meshes with a toothed wheel 730, itself co-operating with a drive element 1000'. Whereas in the first embodiment in FIGS. 2 to 9, the drive element 1000 was connected firstly to the groove 850 of the loading member 800, and secondly directly to the set of teeth 37 of the guide wheel 30, in this embodiment the drive element 1000' is connected firstly to the groove 850 of the loading member 800, as in the first embodiment, but it is connected secondly to the toothed wheel 730 interposed between the drive element 1000' and the guide wheel 30. For the remainder, the operation is similar to the first embodiment, i.e. when the user opens the movable cover elements 11, 12, the drive element 1000' slides in the groove 850, advantageously at a projection 1010'. Since the first groove portion 850 is substantially parallel or equidistant relative to the pivot axis of the movable cover elements 11, 12, the first groove portion does not substantially cause action on the drive element 1000', whereas the second groove portion, of different slope, causes said drive element 1000' to pivot and become disengaged from the toothed wheel 730. If the user closes the device without inhaling, the drive element 1000' merely slides back into the groove 850 and once again becomes meshed with the same tooth of the toothed wheel 730, such that nothing happens to the reservoir substrate or to the blocking means 100. In contrast, after inhalation, when the user closes the movable cover elements, the drive element 1000' becomes meshed in another tooth of the toothed wheel in manner similar to the manner described above for the first embodiment.

FIGS. 27a to 31b show another embodiment in which the reservoir substrate 20 is displaced in the first direction each time the cover elements 11, 12 are opened. In this variant, if the user closes without inhaling, the reservoir substrate is returned to its initial position. In the absence of any inhalation, the reservoir substrate thus moves back and forth so as to return exactly to its start position after closure. Thus, this also guarantees that doses are not lost, even in the event of incomplete manipulation of the device. In the event of inhalation, closure after inhalation does not cause the reservoir substrate to be displaced, so that for the next actuation, it is the next full reservoir that is brought to face the opening means during opening of the cover elements.

In this embodiment, the loading means comprise a rod 1051' that firstly is fastened to the movable support means 50, and that secondly slides by means of a projection 1051" in a groove 1910 that is provided in a loading member 1800, connected to said movable cover elements 11, 12. The loading operation is similar to the loading operation described with reference to FIGS. 10 to 14. The loading member 1800 is meshed with the guide wheel 30, as can be seen more clearly in the views from the rear. Connection means 1000" are provided for co-operating with the guide wheel 30 so long as the movable support means 50 have not been displaced into their dispensing position, after inhalation. After inhalation, the connection means, advantageously including a projection that co-operates with a set of teeth of the guide wheel 30, are deactivated, i.e. they no longer co-operate with the guide wheel. When the user closes the device, the guide wheel together with the movable support means thus return to the non-dispensing position, without turning about the axis of rotation. It is only when fully closed that the connection means once again mesh with the guide wheel.

The device of the invention can also include a dose indicator or counter 120 that is adapted to count or indicate to the user the number of doses that have been dispensed or that remain to be dispensed. In the embodiment shown, the indicator is adapted to count 60 doses. FIGS. 15 to 20 show an actuation cycle of the device and the manner in which the indicator is actuated. The indicator advantageously comprises a ring 127 provided with an inner set of teeth 128 and with an outer set of teeth 129 and including numbers 125, e.g. from 0 to 60, printed on one of its faces. The ring is mounted in such a manner that the numbers pass successively into the window 19 of the body 10. The inner set of teeth 128 is advantageously adapted to co-operate with an actuator 160, whereas the outer set of teeth 129 is advantageously adapted to co-operate with non-return means 170 that are adapted to prevent the indicator ring 127 from turning in the opposite direction to the direction that is imposed thereto by the actuator 160.

Figure 18:
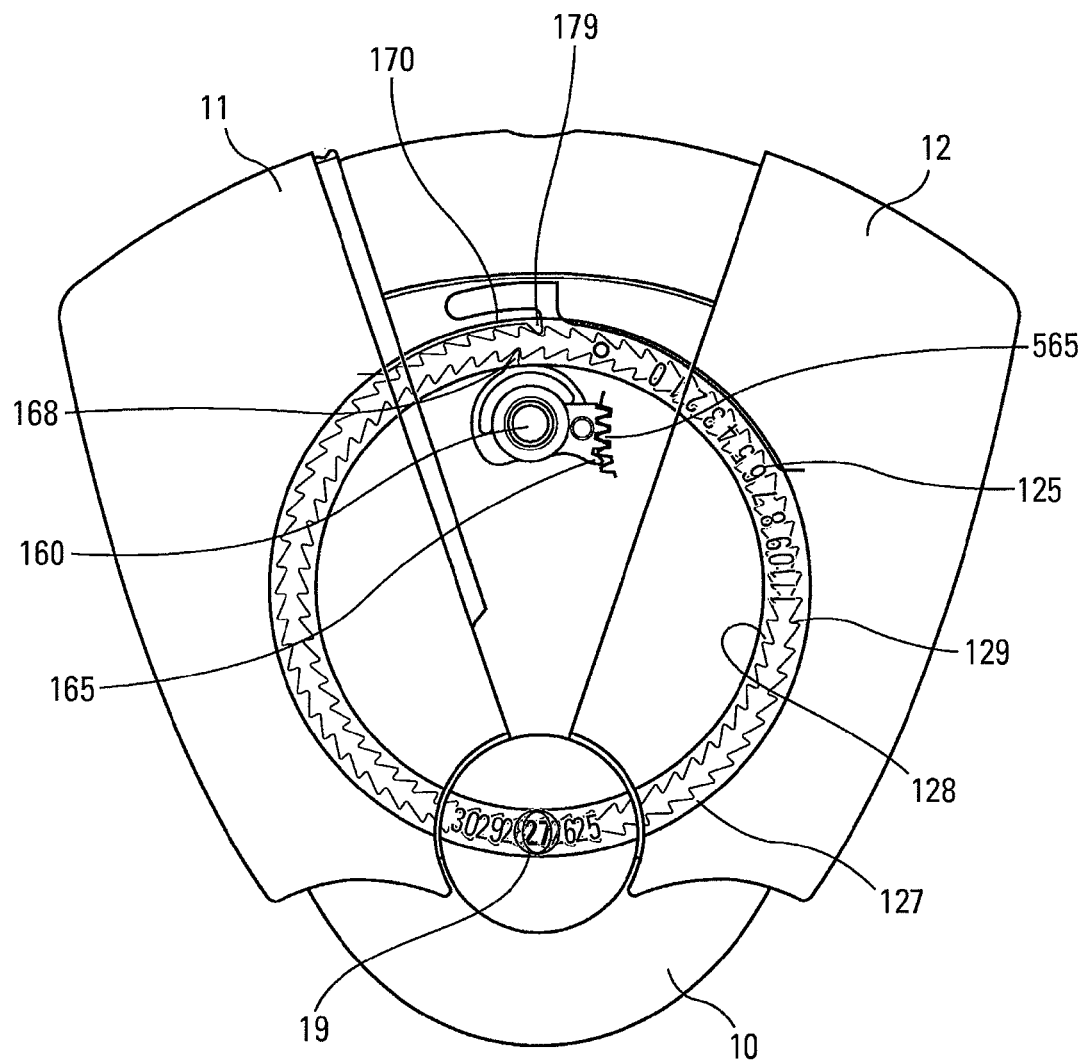
FIG. 18 is a view similar to the view in FIG. 15, shown in the open position.
Figure 19:
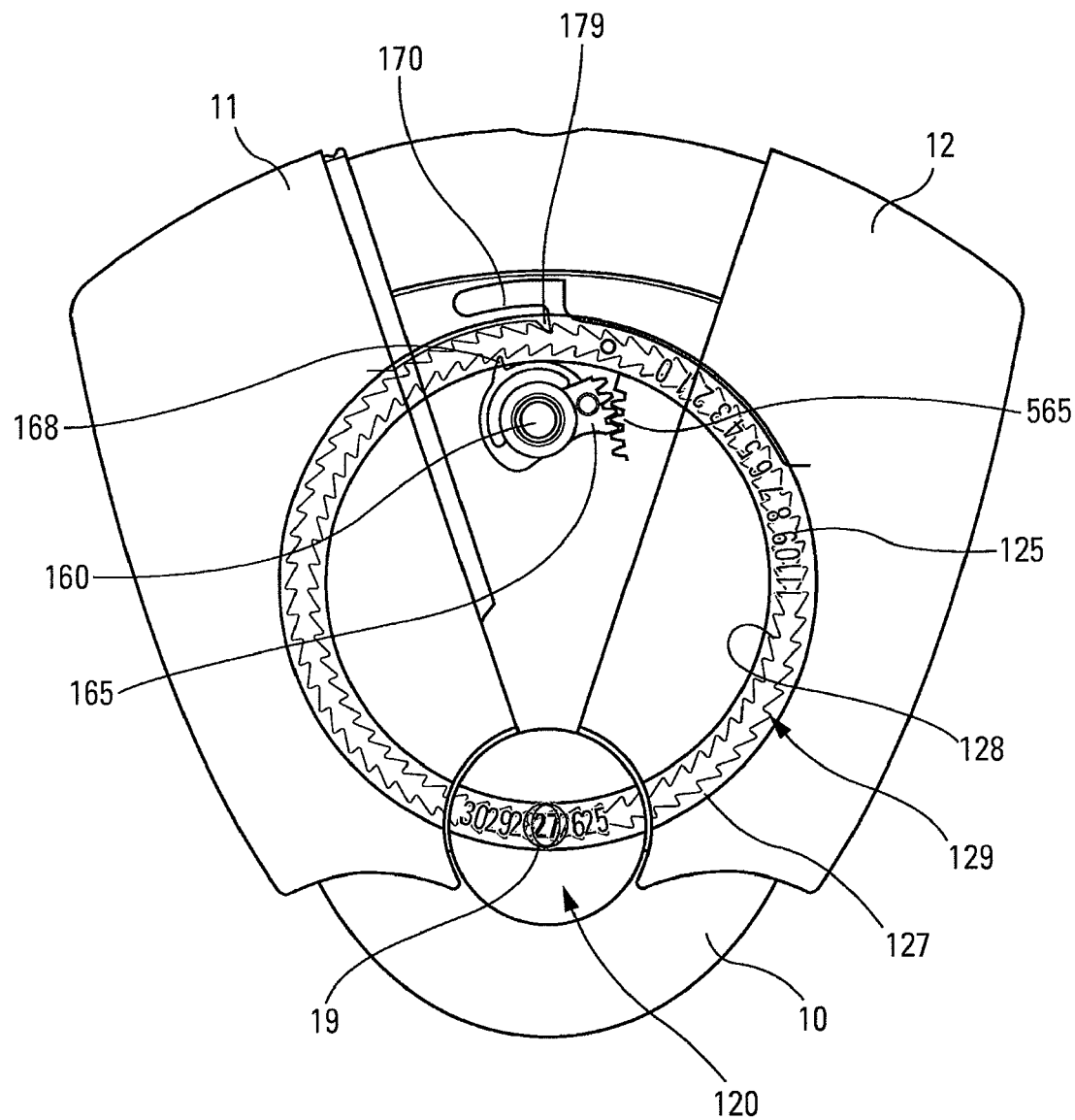
FIG. 19 is a view similar to the view in FIG. 18, shown after inhalation.
Figure 20:
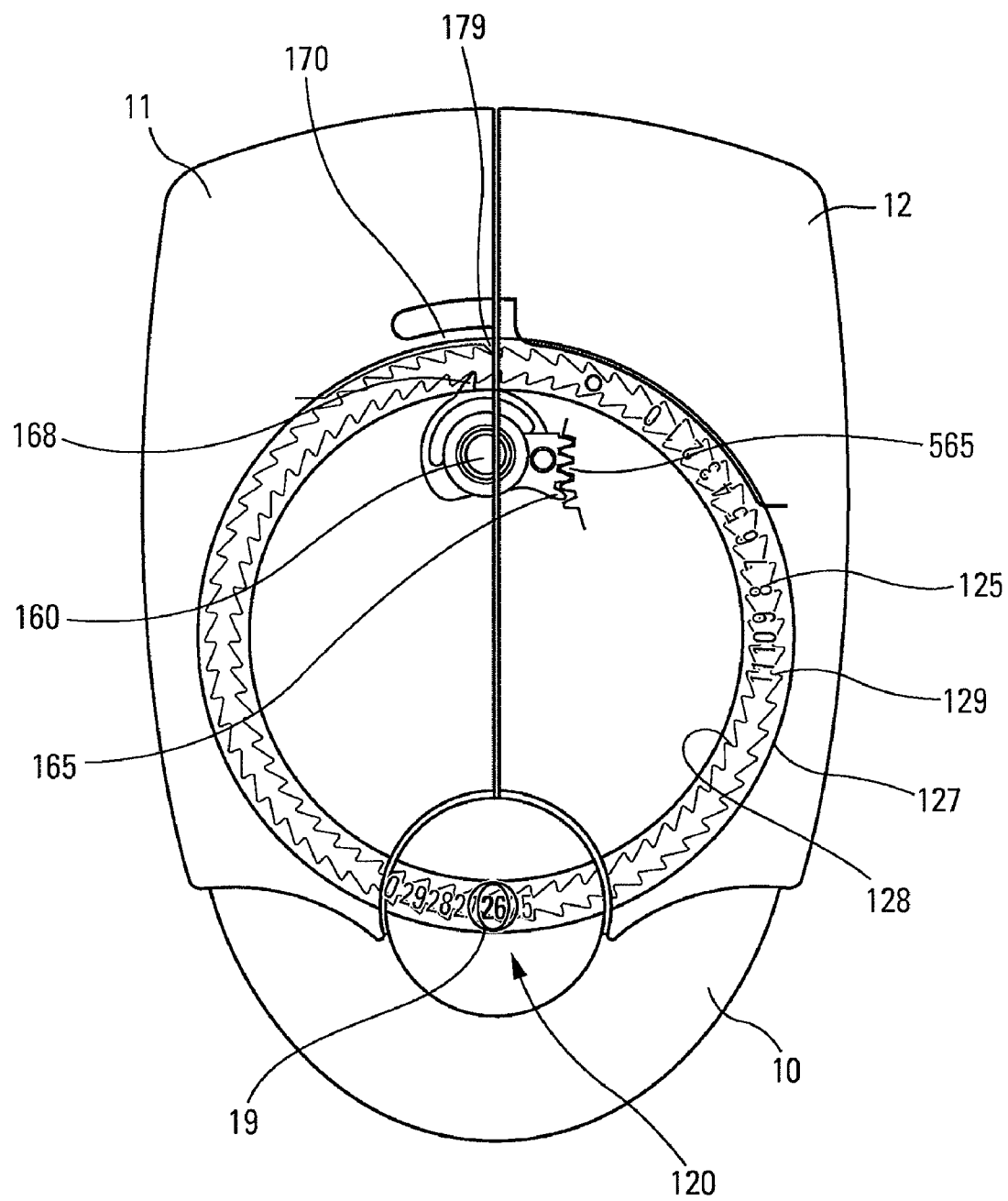
FIG. 20 is a view similar to the view in FIG. 19, shown once closed, after inhalation.
Figure 21:
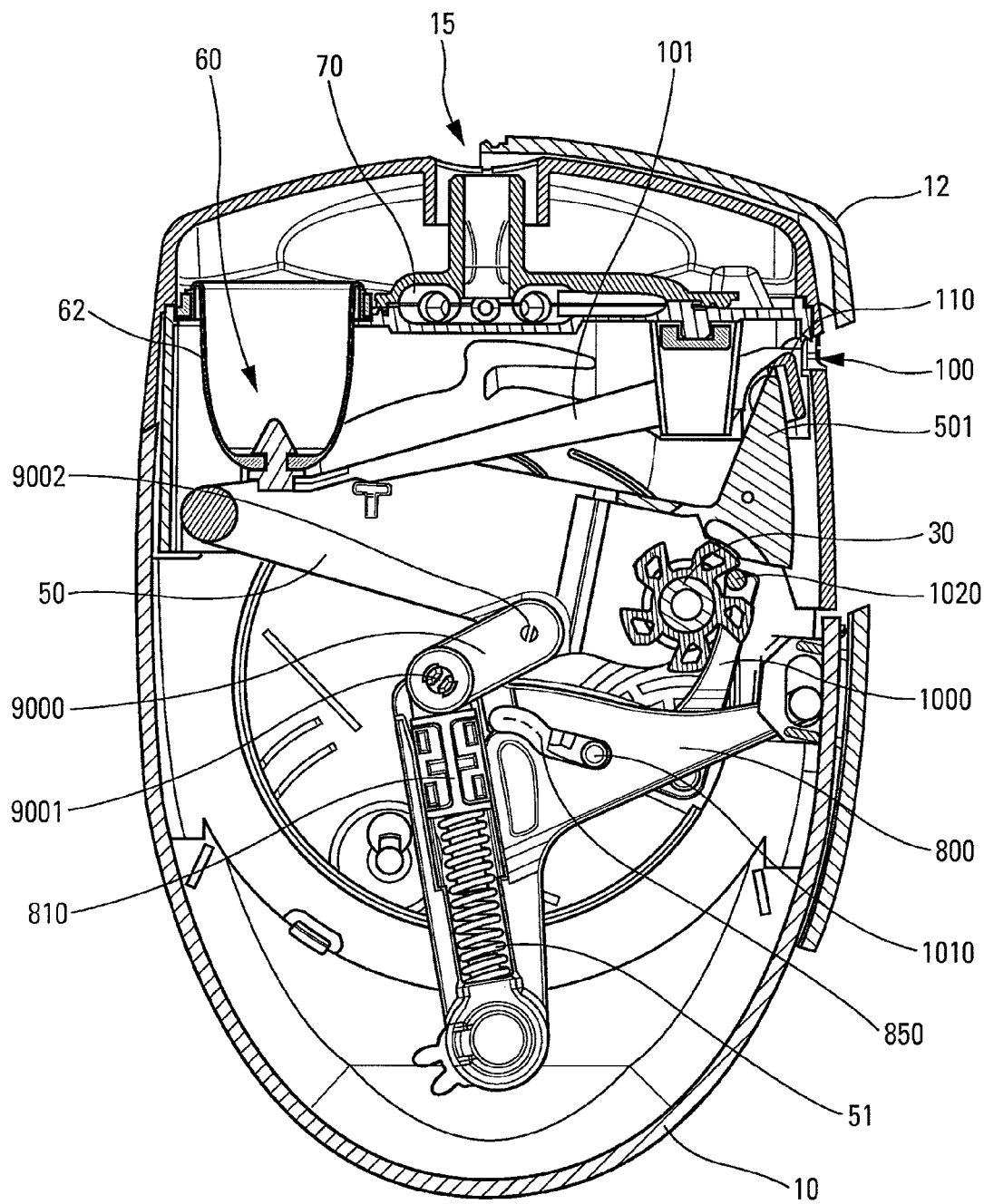
FIG. 21 is a diagrammatic section view of a device constituting another embodiment of the invention, shown in the closed position.

An object of the invention is to avoid counting doses that have not been dispensed, e.g. in the event of a manipulation error, or of an incomplete manipulation of the device. It is thus essential that the counter or indicator is actuated only once the user has inhaled, since it is this inhalation that makes it possible for the blister to open and the dose contained therein to be dispensed. For this purpose, the device includes an actuator 160 that is pivotally mounted on the body 10. The actuator 160 includes engagement means 165, in particular teeth, adapted to mesh in a set of teeth 565, or complementary teeth provided on movable support means 50. Thus, when the user opens the device and loads the loading means of the device, the movable support means 50 do not move since they are held in the non-dispensing position by the blocking means 100. Thus, nothing happens to the indicator since the actuator 160 that is pivotally mounted on the body 10 and meshed with the movable support means 50, also remains stationary. If the user closes the device without inhaling, obviously still nothing happens since the movable support means 50 still remain stationary. In this way, it is guaranteed that the indicator does not count doses if there is no inhalation. From the loaded position, shown in FIG. 18, if the user inhales, the movable support means 50 are displaced into their dispensing position towards the opening means. This displacement thus causes the actuator 160 to pivot in a first direction, as shown in FIGS. 18 and 19. The actuator 160 includes a finger 168 that is meshed in the inner set of teeth 128 of the indicator ring 127. In the first direction of displacement, the finger 168 of the actuator can slide over the slope of the corresponding tooth so as to become positioned facing the next tooth. In parallel, the non-return means 170, in particular a non-return finger 179, co-operate with the outer set of teeth 129 of the ring 127 so as to prevent said ring from turning under the effect of friction, e.g. exerted by the finger 168 of the actuator on the inner set of teeth 128. After inhalation, when the user closes the device, the movable support means 50 are returned to their rest position, i.e. the non-dispensing position. This movement thus causes the actuator 160 to pivot in the direction opposite to the first-described direction, since the respective sets of teeth 165, 565 of the actuator and of the movable support means pivot in the direction opposite to the above-described direction. In the displacement in the opposite direction, the finger 168 of the actuator 160 presses into the tooth in which it is positioned so as to cause the ring 127 to turn, as shown in FIG. 20. In parallel, the non-return finger 179 slides over the slope of the tooth so as to become positioned in the following tooth. In the embodiment shown, the indicator is adapted to indicate the number of doses that remain to be dispensed, so that the number displayed decreases on each actuation. Naturally, the reverse is also possible, i.e. a counter that counts the number of doses that have been dispensed. Advantageously, it is possible to provide blocking means for blocking the indicator after the last dose has been dispensed. The blocking means can take different forms, an advantageous form being to provide a different shaped tooth on the inner set of teeth so that the actuator can no longer become meshed in the next tooth in order to continue causing said indicator ring to turn. Other means of preventing the ring from turning after the last dose has been dispensed can also be envisaged.

In all of the embodiments described above, the blister strip is formed by a strip presenting two ends. In a variant, it is possible to use a continuous strip. Other modifications are also possible without going beyond the ambit of the present invention.

The present invention therefore makes it possible to provide a dry-powder inhaler that performs the following functions:

a plurality of individual doses of powder stored in individual sealed reservoirs, e.g. 30 or 60 doses stored on a rolled-up strip;

the powder is released by perforation that is achieved by the user inhaling, the blister being perforated by means of an inhalation detector system that is coupled to a pre-stressed release system;

appropriately-shaped drive means that are engaged with blisters so as to displace the blister strip on each actuation, and to bring a new reservoir into a position in which it is to be opened by appropriate opening means; and means for avoiding doses being lost in the event of the inhaler being opened, but in the absence of any inhalation. In this event, when the inhaler closes, the device returns exactly to its start position;

a dose indicator adapted to count the doses only in the event of inhalation.

Other functions are also provided by the device of the invention as described above. It should be observed that the various functions, even if they are shown as being provided simultaneously on the various embodiments of the inhaler, could be implemented separately. In particular, the inhalation trigger mechanism could be used regardless of the type of reservoir-opening means, regardless of the use of a dose indicator, regardless of the way in which the individual reservoirs are arranged relative to one another, etc. The prestressing means and the inhalation trigger system could be made in some other way. The same applies for other component parts of the device.

The inhaler of the invention, incorporating all or some of the above-described functions, provides performance that is superior to the performance of existing devices. In particular, the inhaler of the invention preferably provides a reservoir emptying factor of at least 90% on each actuation. The emptying factor, corresponding to the percentage of fluid that is expelled from an open reservoir while the device is being actuated, is advantageously greater than 95%, preferably even greater than 97%. In particular, this high emptying factor is even greater than the performance obtained with active inhalers that are generally more effective than passive inhalers, and in which it is not the inhalation flow that empties the blister and expels the dose but a flow of compressed air that is released while inhaling. The high emptying factor guarantees that the device of the invention is as effective as possible. Coupled with the inhalation-triggered opening, the high emptying factor guarantees that the fluid, specifically the powder, is dispensed in optimum manner into the user's lungs. The invention also provides improved emptying regularity of the reservoirs during successive actuations. Thus, for ten reservoirs of a blister strip, for example, it turns out that the emptying factor varies by less than 15%, advantageously by less than 10%, preferably by less than 5% from one reservoir to another. This improved regularity guarantees improved dose reproducibility, and therefore also improved effectiveness of the device of the invention.

Various modifications can also be envisaged by a person skilled in the art, without going beyond the ambit of the present invention, as defined by the accompanying claims. In particular, the various characteristics and functions of the device described with reference to the various embodiments and variants can be adapted to all of the embodiments and variants, and can be combined together in any appropriate manner.

The invention claimed is:

1. A fluid dispenser device, comprising:
a body provided with a dispenser orifice;
at least one cover element that is movable between a closed position and an open position;
a plurality of individual reservoirs each containing a dose of fluid, said reservoirs being formed on a reservoir substrate;
movable support means that receive said reservoir substrate, and that are displaceable between a non-dispensing position and a dispensing position;
reservoir-opening means for opening a respective reservoir each time said reservoir-opening means are actuated;
displacement means for displacing said reservoir substrate in a first direction so as to bring a full reservoir into register with said reservoir-opening means after each use of the device, said reservoir substrate also being displaceable, together with the movable support means, between said non-dispensing position, in which it said reservoir substrate does not co-operate with said reservoir-opening means, and said dispensing position, in which said reservoir-opening means open a respective reservoir;
loading means for urging said movable support means towards said dispensing position, said loading means being loaded by said at least one cover element;
blocking means for retaining said movable support means in the non-dispensing position;
trigger means for releasing said blocking means and for enabling said movable support means, and thus said reservoir substrate, to be displaced towards said dispensing position, said trigger means being actuated by the user inhaling;
connection means which, when they are activated, connect said displacement means with said at least one cover element, so as to displace said reservoir substrate in said first direction when said at least one cover element is moved between the open and closed positions; and
said connection means being activated while said movable support means are being displaced towards said dispensing position while the user is inhaling, and being deactivated in the absence of any inhalation, such that opening said at least one movable cover and then closing said at least one movable cover without inhaling does not displace said reservoir substrate in said first direction; and
wherein said reservoir-opening means are perforator means that do not move relative to the dispenser orifice and said reservoir substrate is a blister strip, with the reservoirs formed by blisters disposed one behind another along said strip.

2. A device according to claim 1, in which said reservoir substrate co-operates with a guide wheel that includes recesses for receiving said reservoirs, said wheel being displaceable in turning so as to displace said reservoir substrate in said first direction in order to bring a full reservoir into register with the reservoir-opening means at least before or after each inhalation, and being displaceable towards said reservoir-opening means, together with said movable support means in order to open said reservoir, wherein the wheel is displaceable together with said moveable support means when the user inhales.

3. A device according to claim 2, in which said guide wheel is displaceable relative to the reservoir-opening means between a non-dispensing position and a dispensing position in which said reservoir-opening means penetrate into a reservoir, said guide wheel being resiliently urged towards the dispensing position and being retained in the non-dispensing position by blocking means, said blocking means being connected to a pivoting rod that is displaced during inhalation so as to release said blocking means.

4. A device according to claim 2, in which said guide wheel includes a set of teeth that co-operates with a drive element that is connected to at least one movable cover element.

5. A device according to claim 4, in which said connection means engage said set of teeth with said drive element when they are activated, and disengage said first set of teeth from said drive element when they are deactivated.

6. A device according to claim 2, in which a drive element is pivotally mounted on the body, said drive element including a first projection that co-operates with said recessed wheel, and a second projection that co-operates with a loading member that is connected to said at least one movable cover element.

7. A device according to claim 6, in which said loading member is pivotally mounted on the body and includes: engagement means connected to said at least one movable cover element; and guide means for receiving and guiding said second projection of said drive element.

8. A device according to claim 7, in which said groove comprises at least two groove portions, a first portion and a second portion of different inclinations, said drive element being pivoted relative to said body, only while said second projection is co-operating with said second groove portion.

9. A device according to claim 1, in which said reservoir substrate is displaced in said first direction, when the connection means are activated, when said at least one cover element is returned from the open position to the closed position.

10. A device according to claim 1, in which said reservoir substrate is displaced in said first direction, when the connection means are activated, when said at least one cover element is moved from the closed position to the open position.

11. The device according to claim 1, wherein the fluid is a pharmaceutical powder.

12. The device according to claim 7, wherein the guide means is a groove.

13. A fluid dispenser device, comprising:
- a body provided with a dispenser orifice;
- at least one cover element movable between a closed position and an open position;
- a plurality of individual reservoirs each containing a dose of fluid, the reservoirs formed on a reservoir substrate;
- a hinged rigid movable support element that receives the reservoir substrate, and that is displaceable between a non-dispensing position and a dispensing position;
- a perforator or cutter positioned to open a respective reservoir;
- a guide wheel that displaces the reservoir substrate in a first direction so as to bring a full reservoir into register with the perforator or cutter after each use of the device, the reservoir substrate displaceable, together with the hinged rigid movable support element, between the non-dispensing position, in which the reservoir substrate does not co-operate with the perforator or cutter, and the dispensing position, in which the perforator or cutter opens a respective reservoir;
- a resilient element that urges the hinged rigid movable support element towards the dispensing position, the resilient element loaded by the at least one cover element;
- a blocking element cooperating with the hinged rigid movable support element to retain the hinged rigid movable support element in the non-dispensing position;
- a deformable air chamber that releases the blocking element and enables the hinged rigid movable support element and the reservoir substrate to be displaced towards the dispensing position, the deformable air chamber actuated by the user inhaling;
- a drive element which, when activated, connects the guide wheel with the at least one cover element, so as to displace the reservoir substrate in the first direction when the at least one cover element is moved between the open and closed positions; and
- the drive element activated while the hinged rigid movable support element is displaced towards the dispensing position while the user is inhaling, and deactivated in the absence of inhalation, such that opening the at least one movable cover and then closing the at least one movable cover without inhaling does not displace the reservoir substrate in the first direction; and
- wherein the perforator or cutter does not move relative to the dispenser orifice and the reservoir substrate is a blister strip, with the reservoirs formed by blisters disposed linearly one behind another along the strip.

* * * * *